US006815171B2

(12) United States Patent
Burrows et al.

(10) Patent No.: US 6,815,171 B2
(45) Date of Patent: Nov. 9, 2004

(54) RECOMBINANT MHC MOLECULES USEFUL FOR MANIPULATION OF ANTIGEN-SPECIFIC T-CELLS

(75) Inventors: Gregory G. Burrows, Portland, OR (US); Arthur A. Vandenbark, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 54 days.

(21) Appl. No.: 09/858,580

(22) Filed: May 15, 2001

(65) Prior Publication Data

US 2002/0176864 A1 Nov. 28, 2002

Related U.S. Application Data

(63) Continuation of application No. 09/153,586, filed on Sep. 15, 1998, now Pat. No. 6,270,772.
(60) Provisional application No. 60/064,552, filed on Sep. 16, 1997, and provisional application No. 60/064,555, filed on Oct. 10, 1997.

(51) Int. Cl.[7] .......................... G01N 33/53; C12Q 1/02; C07K 14/74
(52) U.S. Cl. ...................... 435/7.24; 435/29; 530/350; 530/403
(58) Field of Search ............................... 530/350, 403; 435/7.24, 29

(56) References Cited

U.S. PATENT DOCUMENTS

| | | |
|---|---|---|
| 5,130,297 A | 7/1992 | Sharma et al. |
| 5,194,425 A | 3/1993 | Sharma et al. |
| 5,260,422 A | 11/1993 | Clark et al. |
| 5,284,935 A | 2/1994 | Clark et al. |
| 5,468,481 A | 11/1995 | Sharma et al. |
| 5,583,031 A | 12/1996 | Stern |
| 5,595,881 A | 1/1997 | Kendrick et al. |
| 5,635,363 A | 6/1997 | Altman et al. |
| 5,734,023 A | 3/1998 | Nag et al. |
| 5,869,270 A | 2/1999 | Rhode et al. |
| 5,976,551 A | 11/1999 | Mottez et al. |
| 6,106,840 A | 8/2000 | Clark et al. |
| 6,232,445 B1 | 5/2001 | Rhode et al. |
| 6,270,772 B1 | 8/2001 | Burrows et al. |
| 2002/0091079 A1 | 7/2002 | Rhode et al. |
| 2002/0198144 A1 | 12/2002 | Wong et al. |

FOREIGN PATENT DOCUMENTS

WO WO95/23814 9/1995

OTHER PUBLICATIONS

Z'hu, Xj et al. European Journal of Immunology (Aug., 1997) 27:1933–1941.*
Altman et al. (1996), Phenotype Analysis of Antigen–Specific T Lymphocytes, *Science*, 274:94–96.
Kozono et al. (1994), Production of Soluble MHC Class II Proteins With Covalently bound Single Peptides, *Nature*, 369:151–154.
Quill & Schwartz (1987), Stimulation of Normal Inducer T Cell Clones with Antigen Presented by Purified Ia Molecules in Planar Lipid Membranes: Specific Induction of a Long–Lived State of Proliferative Nonresponsiveness, *The Journal of Immunology*, 138:3704–3712, No. 11.
Syha et al. (1989), Complete cDNA sequence coding for the MHC class II RT1.B α chain of the Lewis rat, *Nucleic Acids Research*, 17:3985.
Syha–Jedelhauser et al. (1991), Complete coding nucleotide sequence of cDNA for the class II RT1.B $\beta^1$ chain of the Lewis rat, *Biochimica et Biophysica Acta*, 1089:414–416.

* cited by examiner

*Primary Examiner*—Christina Chan
*Assistant Examiner*—F. Pierre VanderVegt
(74) *Attorney, Agent, or Firm*—Klarquist Sparkman, LLP

(57) ABSTRACT

Two-domain MHC polypeptides useful for manipulation of antigen-specific T-cells are disclosed. These polypeptides include MHC class II-based molecules that comprise covalently linked β1 and α1 domains, and MHC class I-based molecules that comprise covalently linked α1 and α2 domains. These polypeptides may also include covalently linked antigenic determinants, toxic moieties, and/or detectable labels. The disclosed polypeptides can be used to target antigen-specific T-cells, and are useful, among other things, to detect and purify antigen-specific T-cells, to induce or activate T-cells, and to treat conditions mediated by antigen-specific T-cells.

14 Claims, 15 Drawing Sheets

```
                    β1α1
         NcoI          ▼
    CCATGGGCAGAGACTCCCCAAGGGATTTCGTGTACCAGTTCAAGGGCCTGTGCTACTACACC
-2  ----------+---------+---------+---------+---------+---------+  60
     M  G  R  D  S  P  R  D  F  V  Y  Q  F  K  G  L  C  Y  Y  T

AACGGGACGCAGCGCATACGGGATGTGATCAGATACATCTACAACCAGGAGGAGTACCTG
61  ----------+---------+---------+---------+---------+---------+  120
     N  G  T  Q  R  I  R  D  V  I  R  Y  I  Y  N  Q  E  E  Y  L

CGCTACGACAGCGACGTGGGCGAGTACCGCGCGCTGACCGAGCTGGGGCGGCCCTCAGCC
121 ----------+---------+---------+---------+---------+---------+  180
     R  Y  D  S  D  V  G  E  Y  R  A  L  T  E  L  G  R  P  S  A
                                                         PstI
    GAGTACTTTAACAAGCAGTACCTGGAGCAGACGCGGGCCGAGCTGGACACGGTCTGCAGA
181 ----------+---------+---------+---------+---------+---------+  240
     E  Y  F  N  K  Q  Y  L  E  Q  T  R  A  E  L  D  T  V  C  R
                                    end of β1 ▼ start of α1
    CACAACTACGAGGGGTCGGAGGTCCGCACCTCCCTGCGGCGGCTTGGAGGTCAAGACGAC
241 ----------+---------+---------+---------+---------+---------+  300
     H  N  Y  E  G  S  E  V  R  T  S  L  R  R  L  G  G  Q  D  D ATTGAGGCCGACCACGTAGCCGCCTATGGTATAAATATGTATCAGTATTATGAATCCAGA
301 ----------+---------+---------+---------+---------+---------+  360
     I  E  A  D  H  V  A  A  Y  G  I  N  M  Y  Q  Y  Y  E  S  R GGCCAGTTCACACATGAATTTGATGGTGACGAGGAATTCTATGTGGACTTGGATAAGAAG
361 ----------+---------+---------+---------+---------+---------+  420
     G  Q  F  T  H  E  F  D  G  D  E  E  F  Y  V  D  L  D  K  K GAGACCATCTGGAGGATCCCCGAGTTTGGACAGCTGACAAGCTTTGACCCCCAAGGTGGA
421 ----------+---------+---------+---------+---------+---------+  480
     E  T  I  W  R  I  P  E  F  G  Q  L  T  S  F  D  P  Q  G  G CTTCAAAATATAGCTATAATAAAACACAATTTGGAAATCTTGATGAAGAGGTCAAATTCA
481 ----------+---------+---------+---------+---------+---------+  540
     L  Q  N  I  A  I  I  K  H  N  L  E  I  L  M  K  R  S  N  S
                    XhoI
    ACCCAAGCTGTCAACTAACTCGAG
541 ----------+---------+----
     T  Q  A  V  N end
```

FIG. 1A

β1α1/MBP-72-89

```
     NcoI                                                                                            SpeI
     CCATGGGCAGAGACTCCCCACAGAAGAGCCAGAGGACTCAGGATGAGAACCCAGTGGTCCACTTCGGAGGTGGAGGCTCCGGTGGGGGCTCCCTTGTCCCCGAGGCTCT
      M  G  R  D  S  P  Q  K  S  Q  R  T  Q  D  E  N  P  V  V  H  F  G  G  G  G  S  G  G  G  G  S  L  V  P  R  G  S
                                                              |---linker---|-----thrombin-----|

GGAGGTGGAGGCTCC
      G  G  G  G  S
     |---linker---|
```

FIG. 1B

β1α1/MBP-55-69

```
     NcoI                                                                                            SpeI
     CCATGGGCAGAGACTCCTCCGGCAAGATTCCCATCATGCCGCGACCCACTACGGTGGAGGTGGAGGCTCACTAGTG
      M  G  R  D  S  S  G  K  D  S  H  H  A  A  R  T  T  H  Y  G  G  G  G  S  L  V
```

```
     NcoI                                                                                            SpeI
     CCATGGGCAGAGACTCCAAACTGGAACTGCAGTCCGCTCTGGAAGAAGCTGAAGCTTCCCTGGAACACGGAGGTGGAGGCTCACTAGTG
      M  G  R  D  S  K  L  E  L  Q  S  A  L  E  E  A  E  A  S  L  E  H  G  G  G  G  S  L  V
```

FIG. 1D

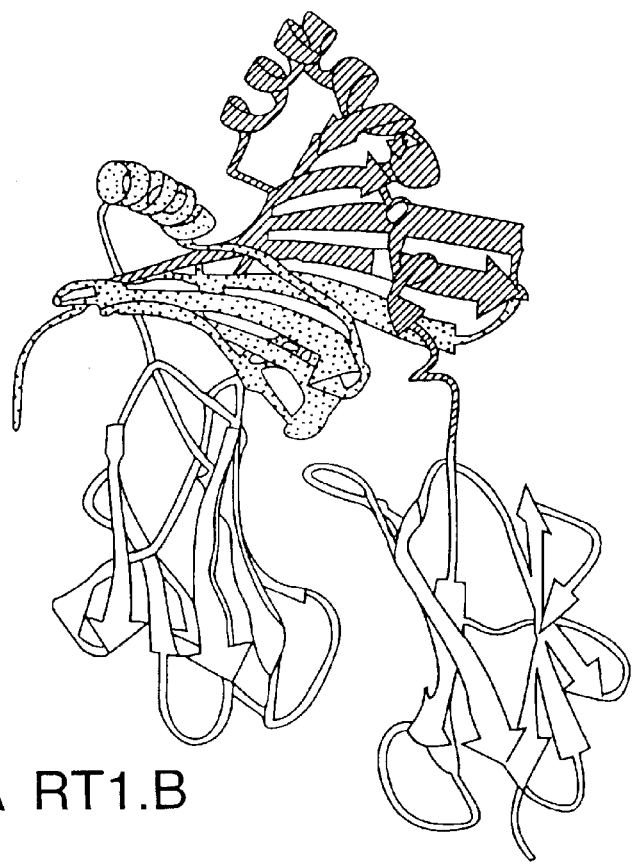
FIG. 2A RT1.B
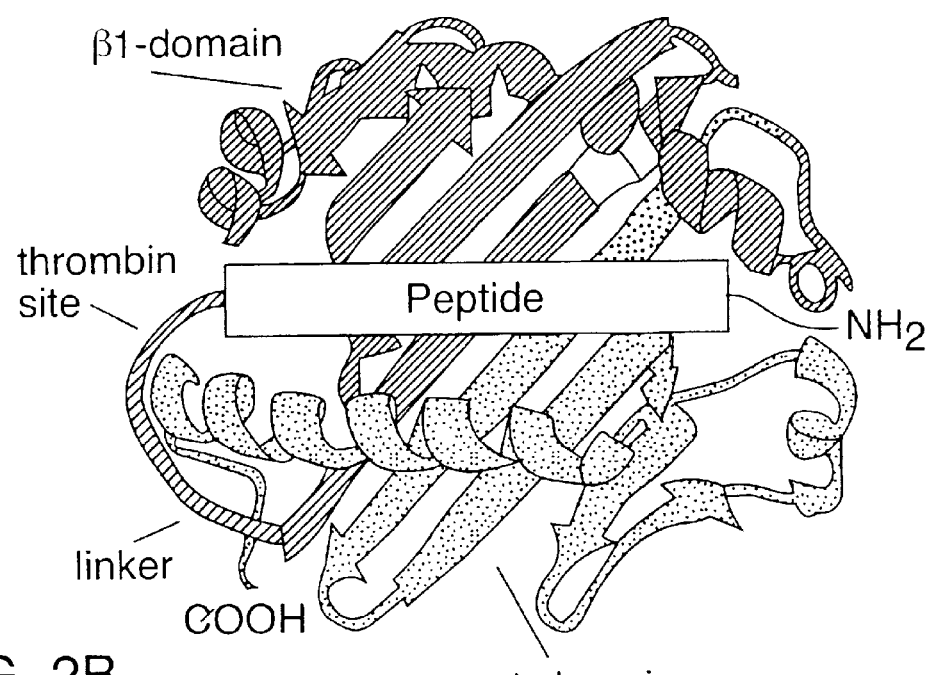
FIG. 2B
β1α1/peptide

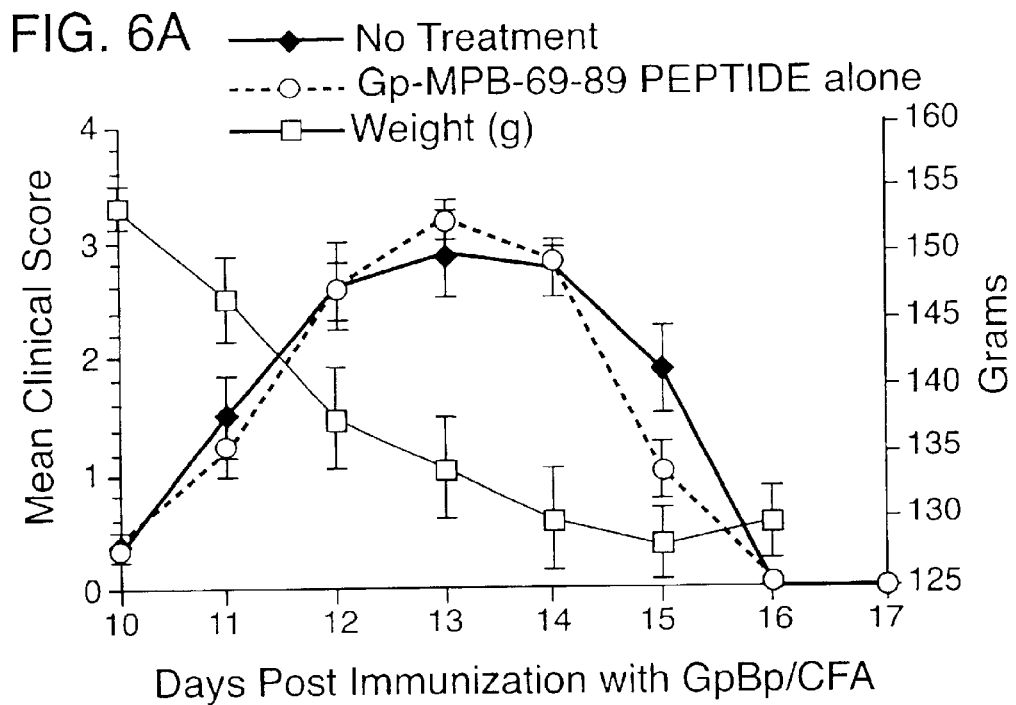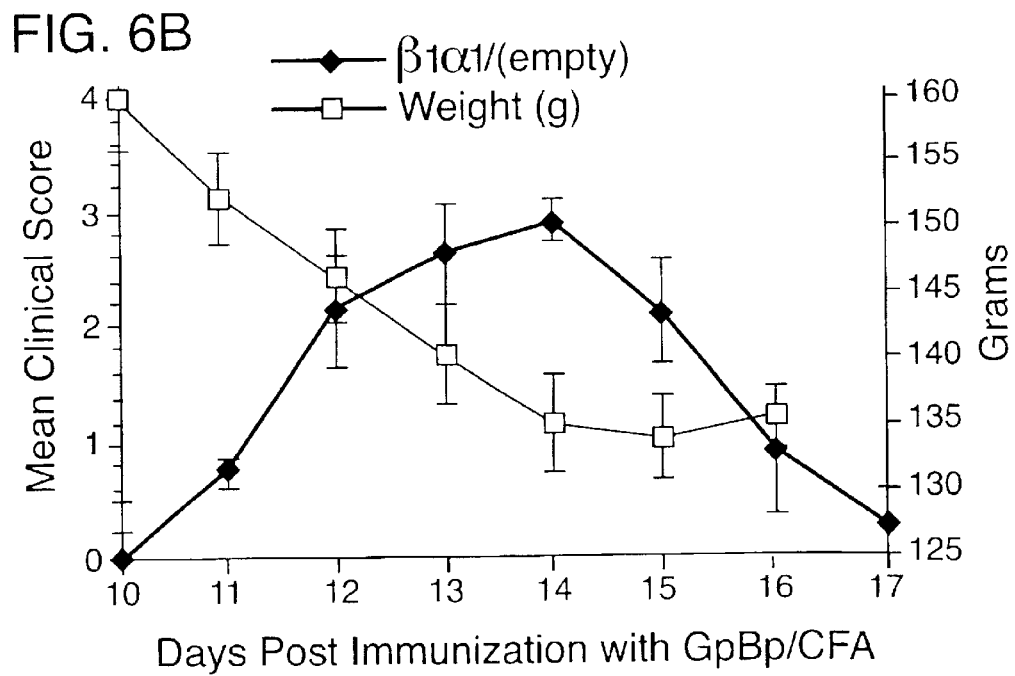

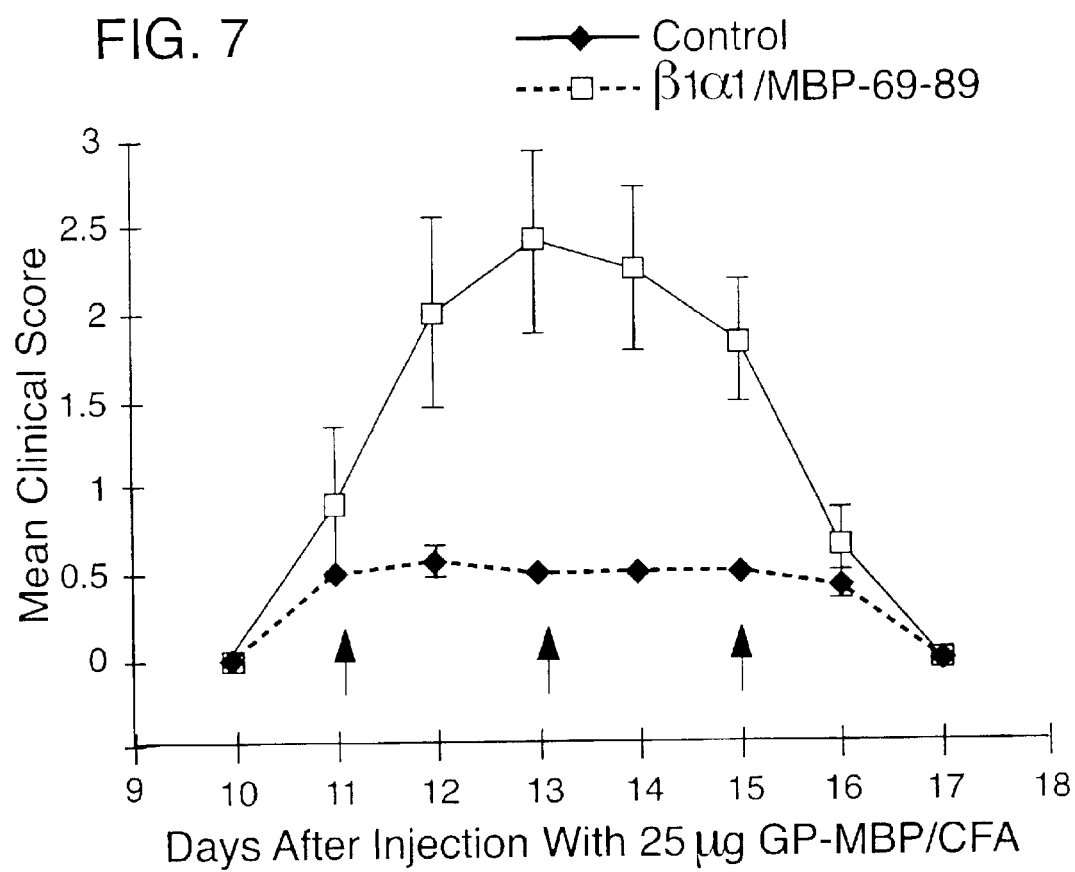

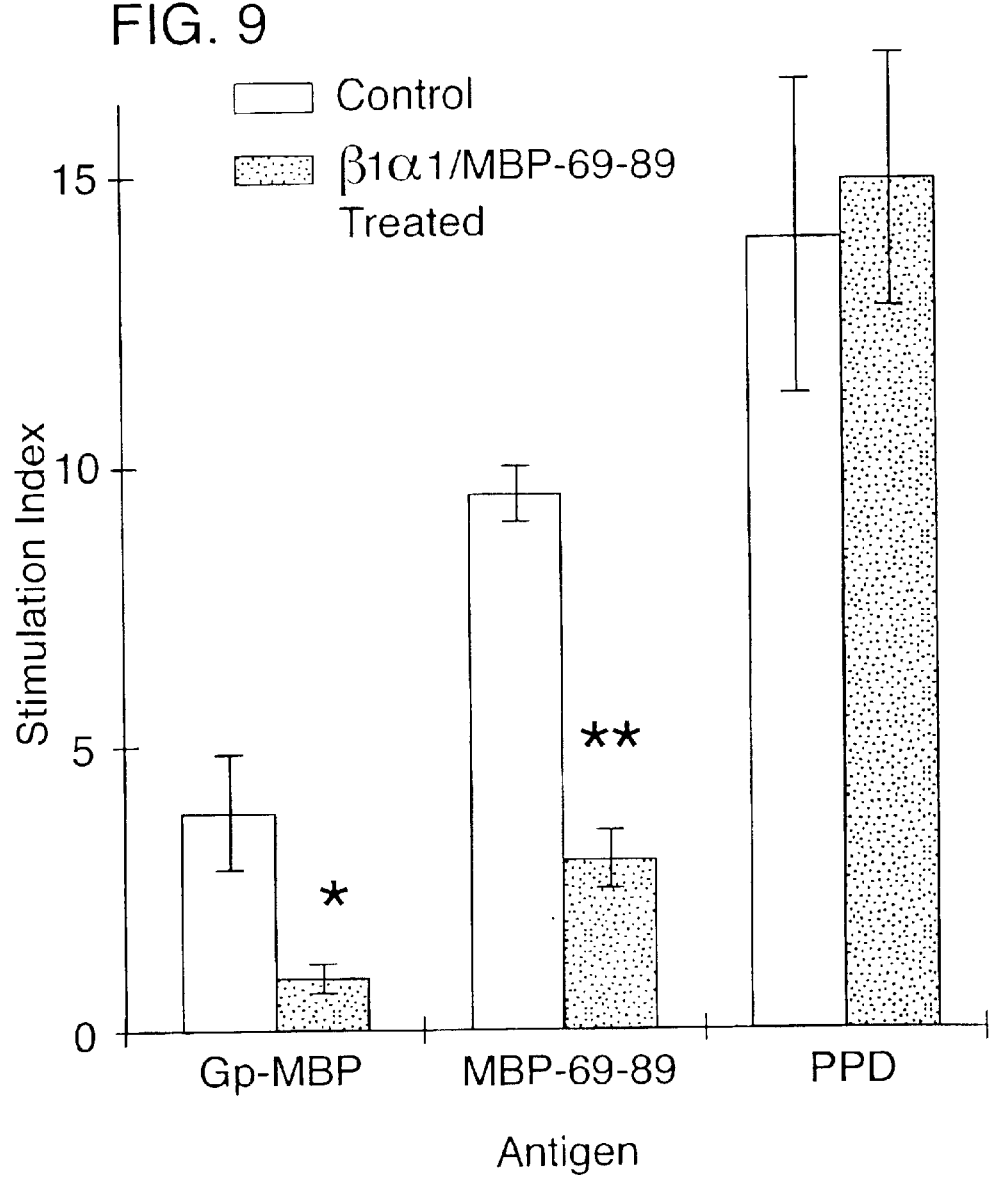

β1 domain:
ARG4-PRO5-ARG6-PHE7-LEU8-TRP9-GLN10-LEU11-LYS12-PHE13-GLU14-CYS15-
HIS16-PHE17-PHE18-ASN19-GLY20-THR21-GLU22-ARG23-VAL24-ARG25-LEU26-
LEU27-GLU28-ARG29-CYS30-ILE31-TYR32-ASN33-GLN34-GLU35-GLU36-SER37-
VAL38-ARG39-PHE40-ASP41-SER42-ASP43-VAL44-GLY45-GLU46-TYR47-ARG48-
ALA49-VAL50-THR51-GLU52-LEU53-GLY54-ARG55-PRO56-ASP57-ALA58-GLU59-
TYR60-TRP61-ASN62-SER63-GLN64-LYS65-ASP66-LEU67-LEU68-GLU69-GLN70-
ARG71-ARG72-ALA73-ALA74-VAL75-ASP76-THR77-TYR78-CYS79-ARG80-HIS81-
ASN82-TYR83-GLY84-VAL85-GLY86-GLU87-SER88-PHE89-THR90-VAL91-GLN92-
ARG93-ARG94-VAL95

α1 domain:
GLU3-GLU4-HIS5-VAL6-ILE7-ILE8-GLN9-ALA10-GLU11-PHE12-TYR13-LEU14-
ASN15-PRO16-ASP17-GLN18-SER19-GLY20-GLU21-PHE22-MET23-PHE24-ASP25-
PHE26-ASP27-GLY28-ASP29-GLU30-ILE31-PHE32-HIS33-VAL34-ASP35-MET36-
ALA37-LYS37-LYS38-LYS39-GLU40-THR41-VAL42-TRP43-ARG44-LEU45-GLU46-GLU47-
PHE48-GLY49-ARG50-PHE51-ALA52-SER53-PHE54-GLU55-ALA56-GLN57-GLY58-
ALA59-LEU60-ALA61-ASN62-ILE63-ALA64-VAL65-ASP66-LYS67-ALA68-ASN69-
LEU70-GLU71-ILE72-MET73-THR74-LYS75-ARG76-SER77-ASN78-TYR79-THR80-
PRO81-ILE82-THR83-ASN84

FIG. 10A

β1 domain:
ARG4-PRO5-TRP6-PHE7-LEU8-GLU9-TYR10-CYS11-LYS12-SER13-GLU14-CYS15-
HIS16-PHE17-TYR18-ASN19-GLY20-THR21-GLN22-ARG23-VAL24-ARG25-LEU26-
LEU27-VAL28-ARG29-TYR30-PHE31-TYR32-ASN33-LEU34-GLU35-GLU36-ASN37-
LEU38-ARG39-PHE40-ASP41-SER42-ASP43-VAL44-GLY45-GLU46-PHE47-ARG48-
ALA49-VAL50-THR51-GLU52-LEU53-GLY54-ARG55-PRO56-ASP57-ALA58-GLU59-
ASN60-TRP61-ASN62-SER63-GLN64-PRO65-GLU66-PHE67-LEU68-GLU69-GLN70-
LYS71-ARG72-ALA73-GLU74-VAL75-ASP76-THR77-VAL78-CYS79-ARG80-HIS81-
ASN82-TYR83-GLU84-ILE85-PHE86-ASP87-ASN88-PHE89-LEU90-VAL91-PRO92-
ARG93-ARG94-VAL95

α1 domain:
GLU3-GLU4-HIS5-THR6-ILE7-ILE8-GLN9-ALA10-GLU11-PHE12-TYR13-LEU14-
LEU15-PRO16-ASP17-LYS18-ARG19-GLY20-GLU21-PHE22-MET23-PHE24-ASP25-
PHE26-ASP27-GLY28-ASP29-GLU30-ILE31-PHE32-HIS33-VAL34-ASP35-ILE36-
GLU37-LYS38-SER39-GLU40-THR41-ILE42-TRP43-ARG44-LEU45-GLU46-GLU47-
PHE48-ALA49-LYS50-PHE51-ALA52-SER53-PHE54-GLU55-ALA56-GLN57-GLY58-
ALA59-LEU60-ALA61-ASN62-ILE63-ALA64-VAL65-ASP66-LYS67-ALA68-ASN69-
LEU70-ASP71-VAL72-MET73-LYS74-GLU75-ARG76-SER77-ASN78-ASN79-THR80-
PRO81-ASP82-ALA83-ASN84

FIG. 10B

β1 domain:
MET(-2)-GLY(-1)-ARG1-ASP2-SER3-PRO4-ARG5-ASP6-PHE7-VAL8-TYR9-
GLN10-PHE11-LYS12-GLY13-LEU14-CYS15-TYR16-TYR17-THR18-ASN19-GLY20-
THR21-GLN22-ARG23-ILE24-ARG25-ASP26-VAL27-ILE28-ARG29-TYR30-ILE31-
TYR32-ASN33-GLN34-GLU35-GLU36-TYR37-LEU38-ARG39-TYR40-ASP41-SER42-
ASP43-VAL44-GLY45-GLU46-TYR47-ARG48-ALA49-LEU50-THR51-GLU52-LEU53-
GLY54-ARG55-PRO56-SER57-ALA58-GLU59-TYR60-TRP61-ASN62-SER63-GLN64-
LYS65-GLN66-TYR67-LEU68-GLU69-GLN70-THR71-ARG72-ALA73-GLU74-LEU75-
ASP76-THR77-VAL78-CYS79-ARG80-HIS81-ASN82-TYR83-GLU84-GLY85-SER86-
GLU87-VAL88-ARG89-THR90-SER91-LEU92-ARG93-ARG94-LEU95

α1 domain:
ALA2-ASP3-HIS4-VAL5-ALA6-ALA7-TYR8-GLY9-ILE10-ASN11-MET12-TYR13-
GLN14-TYR15-TYR16-GLU17-SER18-ARG19-GLY20-GLN21-PHE22-THR23-HIS24-
GLU25-PHE26-ASP27-GLY28-ASP29-GLU30-GLN31-PHE32-TYR33-VAL34-ASP35-
LEU36-ASP37-LYS38-LYS39-GLU40-THR41-ILE42-TRP43-ARG44-ILE45-PRO46-
GLU47-PHE48-GLY49-GLN50-LEU51-THR52-SER53-PHE54-ASP55-PRO56-GLN57-
GLY58-GLY59-LEU60-GLN61-ASN62-ILE63-ALA64-ILE65-ILE66-LYS67-HIS68-
ASN69-LEU70-GLU71-ILE72-LEU73-MET74-LYS75-ARG76-SER77-ASN78-SER79-
THR80-GLN81-ALA82-VAL83-ASN84

FIG. 10C

α1 domain:
GLY1-SER2-HIS3-SER4-MET5-ARG6-TYR7-PHE8-TYR9-THR10-ALA11-MET12-
SER13-ARG14-PRO15-GLY16-ARG17-GLY18-GLU19-PRO20-ARG21-PHE22-ILE23-
ALA24-VAL25-GLY26-TYR27-VAL28-ASP29-ASP30-THR31-GLN32-PHE33-VAL34-
ARG35-PHE36-ASP37-SER38-ASP39-ALA40-ALA41-SER42-PRO43-ARG44-THR45-
GLU46-PRO47-ARG48-PRO49-PRO50-TRP51-ILE52-GLU53-GLN54-GLU55-GLY56-
PRO57-GLU58-TYR59-TRP60-ASP61-ARG62-ASN63-THR64-GLN65-ILE66-PHE67-
LYS68-THR69-ASN70-THR71-GLN72-THR73-TYR74-ARG75-GLU76-ASN77-LEU78-
ARG79-ILE80-ALA81-LEU82-ARG83-TYR84-

α2 domain:
TYR85-ASN86-GLN87-SER88-GLU89-ALA90-GLY91-SER92-HIS93-ILE94-ILE95-
GLN96-ARG97-MET98-TYR99-GLY100-CYS101-ASP102-LEU103-GLY104-PRO105-
ASP106-GLY107-ARG108-LEU109-LEU110-ARG111-GLY112-HIS113-ASP114-
GLN115-SER116-ALA117-TYR118-ASP119-GLY120-LYS121-ASP122-TYR123-
ILE124-ALA125-LEU126-ASN127-GLU128-ASP129-LEU130-SER131-SER132-
TRP133-THR134-ALA135-ASP136-ASP137-THR138-ALA139-ALA140-GLN141-
ILE142-THR143-GLN144-ARG145-LYS146-TRP147-GLU148-ALA149-ALA150-
ARG151-VAL152-ALA153-GLU154-GLN155-LEU156-ARG157-ALA158-TYR159-
LEU160-GLU161-GLY162-LEU163-CYS164-VAL165-GLU166-TRP167-LEU168-
ARG169-TYR170-TYR171-LEU172-GLU173-ASN174-GLY175-LYS176-GLU177-
THR178-LEU179-GLN180-ARG181-ALA182-ASP183-PRO184

FIG. 11

SEQUENCE LISTING

<160> NUMBER OF SEQ ID NOS: 30

<210> SEQ ID NO 1
<211> LENGTH: 566
<212> TYPE: DNA
<213> ORGANISM: Rattus sp.
<220> FEATURE:
<221> NAME/KEY: CDS
<222> LOCATION: (3)..(560)

<400> SEQUENCE: 1

```
cc atg ggc aga gac tcc cca agg gat ttc gtg tac cag ttc aag ggc         47
   Met Gly Arg Asp Ser Pro Arg Asp Phe Val Tyr Gln Phe Lys Gly
   1               5                   10                  15 ctg tgc tac tac acc aac ggg acg cag cgc ata cgg gat gtg atc aga        95
Leu Cys Tyr Tyr Thr Asn Gly Thr Gln Arg Ile Arg Asp Val Ile Arg
                20                  25                  30 tac atc tac aac cag gag gag tac ctg cgc tac gac agc gac gtg ggc       143
Tyr Ile Tyr Asn Gln Glu Glu Tyr Leu Arg Tyr Asp Ser Asp Val Gly
            35                  40                  45 gag tac cgc gcg ctg acc gag ctg ggg cgg ccc tca gcc gag tac ttt       191
Glu Tyr Arg Ala Leu Thr Glu Leu Gly Arg Pro Ser Ala Glu Tyr Phe
        50                  55                  60 aac aag cag tac ctg gag cag acg cgg gcc gag ctg gac acg gtc tgc       239
Asn Lys Gln Tyr Leu Glu Gln Thr Arg Ala Glu Leu Asp Thr Val Cys
 65                  70                  75 aga cac aac tac gag ggg tcg gag gtc cgc acc tcc ctg cgg cgg ctt       287
Arg His Asn Tyr Glu Gly Ser Glu Val Arg Thr Ser Leu Arg Arg Leu
 80                  85                  90                  95 gga ggt caa gac gac att gag gcc gac cac gta gcc gcc tat ggt ata       335
Gly Gly Gln Asp Asp Ile Glu Ala Asp His Val Ala Ala Tyr Gly Ile
                100                 105                 110 aat atg tat cag tat tat gaa tcc aga ggc cag ttc aca cat gaa ttt       383
Asn Met Tyr Gln Tyr Tyr Glu Ser Arg Gly Gln Phe Thr His Glu Phe
            115                 120                 125 gat ggt gac gag gaa ttc tat gtg gac ttg gat aag aag gag acc atc       431
Asp Gly Asp Glu Glu Phe Tyr Val Asp Leu Asp Lys Lys Glu Thr Ile
        130                 135                 140 tgg agg atc ccc gag ttt gga cag ctg aca agc ttt gac ccc caa ggt       479
Trp Arg Ile Pro Glu Phe Gly Gln Leu Thr Ser Phe Asp Pro Gln Gly
    145                 150                 155 gga ctt caa aat ata gct ata ata aaa cac aat ttg gaa atc ttg atg       527
Gly Leu Gln Asn Ile Ala Ile Ile Lys His Asn Leu Glu Ile Leu Met
160                 165                 170                 175 aag agg tca aat tca acc caa gct gtc aac taa ctcgag                    566
Lys Arg Ser Asn Ser Thr Gln Ala Val Asn
                180                 185
```

<210> SEQ ID NO 2
<211> LENGTH: 185
<212> TYPE: PRT
<213> ORGANISM: Rattus sp.

<400> SEQUENCE: 2

```
Met Gly Arg Asp Ser Pro Arg Asp Phe Val Tyr Gln Phe Lys Gly Leu
1               5                   10                  15

Cys Tyr Tyr Thr Asn Gly Thr Gln Arg Ile Arg Asp Val Ile Arg Tyr
            20                  25                  30

Ile Tyr Asn Gln Glu Glu Tyr Leu Arg Tyr Asp Ser Asp Val Gly Glu
        35                  40                  45
```

```
Tyr Arg Ala Leu Thr Glu Leu Gly Arg Pro Ser Ala Glu Tyr Phe Asn
         50                  55                  60

Lys Gln Tyr Leu Glu Gln Thr Arg Ala Glu Leu Asp Thr Val Cys Arg
 65                  70                  75                  80

His Asn Tyr Glu Gly Ser Glu Val Arg Thr Ser Leu Arg Arg Leu Gly
                 85                  90                  95

Gly Gln Asp Asp Ile Glu Ala Asp His Val Ala Ala Tyr Gly Ile Asn
            100                 105                 110

Met Tyr Gln Tyr Tyr Glu Ser Arg Gly Gln Phe Thr His Glu Phe Asp
            115                 120                 125

Gly Asp Glu Glu Phe Tyr Val Asp Leu Asp Lys Lys Glu Thr Ile Trp
130                 135                 140

Arg Ile Pro Glu Phe Gly Gln Leu Thr Ser Phe Asp Pro Gln Gly Gly
145                 150                 155                 160

Leu Gln Asn Ile Ala Ile Ile Lys His Asn Leu Glu Ile Leu Met Lys
                165                 170                 175

Arg Ser Asn Ser Thr Gln Ala Val Asn
            180                 185

<210> SEQ ID NO 3
<211> LENGTH: 113
<212> TYPE: DNA
<213> ORGANISM: Artificial Sequence
<220> FEATURE:
<221> NAME/KEY: CDS
<222> LOCATION: (3)..(113)
<223> OTHER INFORMATION: Description of Artificial Sequence: antigen/
      linker insert

<400> SEQUENCE: 3 cc atg ggc aga gac tcc cca cag aag agc cag agg act cag gat gag       47
   Met Gly Arg Asp Ser Pro Gln Lys Ser Gln Arg Thr Gln Asp Glu
    1               5                  10                  15 aac cca gtg gtg cac ttc gga ggt gga ggc tca cta gtg ccc cga ggc      95
Asn Pro Val Val His Phe Gly Gly Gly Gly Ser Leu Val Pro Arg Gly
             20                  25                  30 tct gga ggt gga ggc tcc                                             113
Ser Gly Gly Gly Gly Ser
            35

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: antigen/
      linker insert

<400> SEQUENCE: 4

Met Gly Arg Asp Ser Pro Gln Lys Ser Gln Arg Thr Gln Asp Glu Asn
 1               5                  10                  15

Pro Val Val His Phe Gly Gly Gly Gly Ser Leu Val Pro Arg Gly Ser
             20                  25                  30

Gly Gly Gly Gly Ser
            35

<210> SEQ ID NO 5
<211> LENGTH: 83
<212> TYPE: DNA
<213> ORGANISM: Artificial Sequence
<220> FEATURE:
```

```
<221> NAME/KEY: CDS
<222> LOCATION: (3)..(83)
<223> OTHER INFORMATION: Description of Artificial Sequence: alternative
      antigen encoding sequences for the expression cassette

<400> SEQUENCE: 5 cc atg ggc aga gac tcc tcc ggc aag gat tcg cat cat gcg gcg cgg         47
   Met Gly Arg Asp Ser Ser Gly Lys Asp Ser His His Ala Ala Arg
    1               5                  10                  15 acg acc cac tac ggt gga ggt gga ggc tca cta gtg                        83
Thr Thr His Tyr Gly Gly Gly Gly Gly Ser Leu Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: alternative
      antigen encoding sequences for the expression cassette

<400> SEQUENCE: 6

Met Gly Arg Asp Ser Ser Gly Lys Asp Ser His His Ala Ala Arg Thr
 1               5                  10                  15

Thr His Tyr Gly Gly Gly Gly Gly Ser Leu Val
            20                  25

<210> SEQ ID NO 7
<211> LENGTH: 89
<212> TYPE: DNA
<213> ORGANISM: Artificial Sequence
<220> FEATURE:
<221> NAME/KEY: CDS
<222> LOCATION: (3)..(89)
<223> OTHER INFORMATION: Description of Artificial Sequence: alternative
      antigen encoding sequences for the expression cassette

<400> SEQUENCE: 7 cc atg ggc aga gac tcc aaa ctg gaa ctg cag tcc gct ctg gaa gaa         47
   Met Gly Arg Asp Ser Lys Leu Glu Leu Gln Ser Ala Leu Glu Glu
    1               5                  10                  15 gct gaa gct tcc ctg gaa cac gga ggt gga ggc tca cta gtg                89
Ala Glu Ala Ser Leu Glu His Gly Gly Gly Gly Ser Leu Val
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: alternative
      antigen encoding sequences for the expression cassette

<400> SEQUENCE: 8

Met Gly Arg Asp Ser Lys Leu Glu Leu Gln Ser Ala Leu Glu Glu Ala
 1               5                  10                  15

Glu Ala Ser Leu Glu His Gly Gly Gly Gly Ser Leu Val
            20                  25

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 9
```

-continued

```
aattcctcga gatggctctg cagacccc                                          28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 10
tcttgacctc caagccgccg cagggaggtg                                        30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 11
cggcggcttg gaggtcaaga cgacattgag g                                      31

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 12
gcctcggtac cttagttgac agcttgggtt gaatttg                                37

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 13
cagggaccat gggcagagac tcccca                                            26

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 14
gcctcctcga gttagttgac agcttgggtt                                        30

<210> SEQ ID NO 15
<211> LENGTH: 128
<212> TYPE: DNA
<213> ORGANISM: Artificial Sequence
<220> FEATURE:
<223> OTHER INFORMATION: Description of Artificial Sequence: PCR primer

<400> SEQUENCE: 15
gaaatcccgc ggggagcctc cacctccaga gcctcggggc actagtgagc ctccacctcc       60
gaagtgcacc actgggttct catcctgagt cctctggctc ttctgtgggg agtctctgcc      120
ctcagtcc                                                               128
```

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 16
gctccccgcg ggatttcgtg taccagttca a    31

<210> SEQ ID NO 17
<211> LENGTH: 92
<212> TYPE: DNA
<213> ORGANISM: Artificial Sequence
<220> FEATURE:
<223> OTHER INFORMATION: Description of Artificial Sequence: PCR primer

<400> SEQUENCE: 17
tattaccatg ggcagagact cctccggcaa ggattcgcat catgcggcgc ggacgaccca    60
ctacggtgga ggtggaggct cactagtgcc cc    92

<210> SEQ ID NO 18
<211> LENGTH: 92
<212> TYPE: DNA
<213> ORGANISM: Artificial Sequence
<220> FEATURE:
<223> OTHER INFORMATION: Description of Artificial Sequence: PCR primer

<400> SEQUENCE: 18
ggggcactag tgagcctcca cctccaccgt agtgggtcgt ccgcgccgca tgatgcgaat    60
ccttgccgga ggagtctctg cccatggtaa ta    92

<210> SEQ ID NO 19
<211> LENGTH: 98
<212> TYPE: DNA
<213> ORGANISM: Artificial Sequence
<220> FEATURE:
<223> OTHER INFORMATION: Description of Artificial Sequence: PCR primer

<400> SEQUENCE: 19
tattaccatg ggcagagact ccaaactgga actgcagtcc gctctggaag aagctgaagc    60
ttccctggaa cacggaggtg gaggctcact agtgcccc    98

<210> SEQ ID NO 20
<211> LENGTH: 98
<212> TYPE: DNA
<213> ORGANISM: Artificial Sequence
<220> FEATURE:
<223> OTHER INFORMATION: Description of Artificial Sequence: PCR primer

<400> SEQUENCE: 20
ggggcactag tgagcctcca cctccgtgtt ccagggaagc ttcagcttct tccagagcgg    60
actgcagttc cagtttggag tctctgccca tggtaata    98

<210> SEQ ID NO 21
<211> LENGTH: 184
<212> TYPE: PRT
<213> ORGANISM: Homo sapiens

<400> SEQUENCE: 21

Gly Ser His Ser Met Arg Tyr Phe Tyr Thr Ala Met Ser Arg Pro Gly
 1               5                  10                  15

-continued

```
Arg Gly Glu Pro Arg Phe Ile Ala Val Gly Tyr Val Asp Asp Thr Gln
            20                  25                  30
Phe Val Arg Phe Asp Ser Asp Ala Ala Ser Pro Arg Thr Glu Pro Arg
        35                  40                  45
Pro Pro Trp Ile Glu Gln Glu Gly Pro Glu Tyr Trp Asp Arg Asn Thr
    50                  55                  60
Gln Ile Phe Lys Thr Asn Thr Gln Thr Tyr Arg Glu Asn Leu Arg Ile
65                  70                  75                  80
Ala Leu Arg Tyr Tyr Asn Gln Ser Glu Ala Gly Ser His Ile Ile Gln
                85                  90                  95
Arg Met Tyr Gly Cys Asp Leu Gly Pro Asp Gly Arg Leu Leu Arg Gly
            100                 105                 110
His Asp Gln Ser Ala Tyr Asp Gly Lys Asp Tyr Ile Ala Leu Asn Glu
        115                 120                 125
Asp Leu Ser Ser Trp Thr Ala Ala Asp Thr Ala Ala Gln Ile Thr Gln
    130                 135                 140
Arg Lys Trp Glu Ala Ala Arg Val Ala Glu Gln Leu Arg Ala Tyr Leu
145                 150                 155                 160
Glu Gly Leu Cys Val Glu Trp Leu Arg Arg Tyr Leu Glu Asn Gly Lys
                165                 170                 175
Glu Thr Leu Gln Arg Ala Asp Pro
            180

<210> SEQ ID NO 22
<211> LENGTH: 174
<212> TYPE: PRT
<213> ORGANISM: Homo sapiens

<400> SEQUENCE: 22

Arg Pro Arg Phe Leu Trp Gln Leu Lys Phe Glu Cys His Phe Phe Asn
1               5                   10                  15
Gly Thr Glu Arg Val Arg Leu Leu Glu Arg Cys Ile Tyr Asn Gln Glu
            20                  25                  30
Glu Ser Val Arg Phe Asp Ser Asp Val Gly Glu Tyr Arg Ala Val Thr
        35                  40                  45
Glu Leu Gly Arg Pro Asp Ala Glu Tyr Trp Asn Ser Gln Lys Asp Leu
    50                  55                  60
Leu Glu Gln Arg Arg Ala Ala Val Asp Thr Tyr Cys Arg His Asn Tyr
65                  70                  75                  80
Gly Val Gly Glu Ser Phe Thr Val Gln Arg Arg Val Glu Glu His Val
                85                  90                  95
Ile Ile Gln Ala Glu Phe Tyr Leu Asn Pro Asp Gln Ser Gly Glu Phe
            100                 105                 110
Met Phe Asp Phe Asp Gly Asp Glu Ile Phe His Val Asp Met Ala Lys
        115                 120                 125
Lys Glu Thr Val Trp Arg Leu Glu Glu Phe Gly Arg Phe Ala Ser Phe
    130                 135                 140
Glu Ala Gln Gly Ala Leu Ala Asn Ile Ala Val Asp Lys Ala Asn Leu
145                 150                 155                 160
Glu Ile Met Thr Lys Arg Ser Asn Tyr Thr Pro Ile Thr Asn
                165                 170

<210> SEQ ID NO 23
<211> LENGTH: 174
<212> TYPE: PRT
<213> ORGANISM: Mus sp.
```

```
<400> SEQUENCE: 23

Arg Pro Trp Phe Leu Glu Tyr Cys Lys Ser Glu Cys His Phe Tyr Asn
  1               5                  10                  15

Gly Thr Gln Arg Val Arg Leu Val Arg Tyr Phe Tyr Asn Leu Glu
             20                  25                  30

Glu Asn Leu Arg Phe Asp Ser Asp Val Gly Glu Phe Arg Ala Val Thr
         35                  40                  45

Glu Leu Gly Arg Pro Asp Ala Glu Asn Trp Asn Ser Gln Pro Glu Phe
 50                  55                  60

Leu Glu Gln Lys Arg Ala Glu Val Asp Thr Val Cys Arg His Asn Tyr
 65                  70                  75                  80

Glu Ile Phe Asp Asn Phe Leu Val Pro Arg Arg Val Glu Glu His Thr
                 85                  90                  95

Ile Ile Gln Ala Glu Phe Tyr Leu Leu Pro Asp Lys Arg Gly Glu Phe
                100                 105                 110

Met Phe Asp Phe Asp Gly Asp Glu Ile Phe His Val Asp Ile Glu Lys
            115                 120                 125

Ser Glu Thr Ile Trp Arg Leu Glu Glu Phe Ala Lys Phe Ala Ser Phe
130                 135                 140

Glu Ala Gln Gly Ala Leu Ala Asn Ile Ala Val Asp Lys Ala Asn Leu
145                 150                 155                 160

Asp Val Met Lys Glu Arg Ser Asn Asn Thr Pro Asp Ala Asn
                165                 170

<210> SEQ ID NO 24
<211> LENGTH: 180
<212> TYPE: PRT
<213> ORGANISM: Rattus sp.

<400> SEQUENCE: 24

Met Gly Arg Asp Ser Pro Arg Asp Phe Val Tyr Gln Phe Lys Gly Leu
  1               5                  10                  15

Cys Tyr Tyr Thr Asn Gly Thr Gln Arg Ile Arg Asp Val Ile Arg Tyr
             20                  25                  30

Ile Tyr Asn Gln Glu Glu Tyr Leu Arg Tyr Asp Ser Asp Val Gly Glu
         35                  40                  45

Tyr Arg Ala Leu Thr Glu Leu Gly Arg Pro Ser Ala Glu Tyr Trp Asn
 50                  55                  60

Ser Gln Lys Gln Tyr Leu Glu Gln Thr Arg Ala Glu Leu Asp Thr Val
 65                  70                  75                  80

Cys Arg His Asn Tyr Glu Gly Ser Glu Val Arg Thr Ser Leu Arg Arg
                 85                  90                  95

Leu Ala Asp His Val Ala Ala Tyr Gly Ile Asn Met Tyr Gln Tyr Tyr
                100                 105                 110

Glu Ser Arg Gly Gln Phe Thr His Glu Phe Asp Gly Asp Glu Glu Phe
            115                 120                 125

Tyr Val Asp Leu Asp Lys Lys Glu Thr Ile Trp Arg Ile Pro Glu Phe
130                 135                 140

Gly Gln Leu Thr Ser Phe Asp Pro Gln Gly Gly Leu Gln Asn Ile Ala
145                 150                 155                 160

Ile Ile Lys His Asn Leu Glu Ile Leu Met Lys Arg Ser Asn Ser Thr
                165                 170                 175

Gln Ala Val Asn
            180
```

```
<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: artificial
      peptide

<400> SEQUENCE: 25

Gly Ser Leu Pro Gln Lys Ser Gln Arg Ser Gln Asp Glu Asn Pro Val
  1               5                  10                  15

Val His Phe

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: artificial
      peptide

<400> SEQUENCE: 26

Ser Gly Lys Asp Ser His His Ala Ala Arg Thr Thr His Tyr Gly
  1               5                  10                  15

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: artificial
      peptide

<400> SEQUENCE: 27

Lys Leu Glu Leu Gln Ser Ala Leu Glu Glu Ala Glu Ala Ser Leu Glu
  1               5                  10                  15

His

<210> SEQ ID NO 28
<211> LENGTH: 95
<212> TYPE: DNA
<213> ORGANISM: Artificial Sequence
<220> FEATURE:
<223> OTHER INFORMATION: Description of Artificial Sequence: PCR primer

<400> SEQUENCE: 28
tattaccatg ggcagagact ccccacagaa gagccagagg tctcaggatg agaacccagt    60
ggtgcacttc ggaggtggag gctcactagt gcccc                              95

<210> SEQ ID NO 29
<211> LENGTH: 94
<212> TYPE: DNA
<213> ORGANISM: Artificial Sequence
<220> FEATURE:
<223> OTHER INFORMATION: Description of Artificial Sequence: PCR primer

<400> SEQUENCE: 29
ggggcactag tgagcctcca cctccgaagt gcaccactgg gttctcatcc tgagacctct    60
ggctcttctg tggggagtct ctgcccatgg taat                               94

<210> SEQ ID NO 30
<211> LENGTH: 19
<212> TYPE: PRT
```

```
<213> ORGANISM: Artificial Sequence
<220> FEATURE:
<223> OTHER INFORMATION: Description of Artificial Sequence: artificial
      peptide

<400> SEQUENCE: 30

Gly Ser Leu Pro Gln Lys Ser Gln Arg Thr Gln Asp Glu Asn Pro Val
 1               5                  10                  15

Val His Phe
```

RECOMBINANT MHC MOLECULES USEFUL FOR MANIPULATION OF ANTIGEN-SPECIFIC T-CELLS

PRIORITY CLAIM

This is a continuation of U.S. patent application Ser. No. 09/153,586, filed Sep. 15, 1998, which issued as U.S. Pat. No. 6,270,772, which claims the benefit of U.S. Provisional Application No. 60/064,552 and U.S. Provisional Application No. 60/064,555, filed Sep. 16, 1997 and Oct. 10, 1997, respectively, all of which are incorporated herein by reference.

BACKGROUND OF THE INVENTION

The initiation of an immune response against a specific antigen in mammals is brought about by the presentation of that antigen to T-cells. An antigen is presented to T-cells in the context of a major histocompatibility (MHC) complex. MHC complexes are located on the surface of antigen presenting cells (APCs); the 3-dimensional structure of MHCs includes a groove or cleft into which the presented antigen fits. When an appropriate receptor on a T-cell interacts with the MHC/antigen complex on an APC in the presence of necessary co-stimulatory signals, the T-cell is stimulated, triggering various aspects of the well characterized cascade of immune system activation events, including induction of cytotoxic T-cell function, induction of B-cell function and stimulation of cytokine production.

There are two basic classes of MHC molecules in mammals, MHC class I and MHC II. Both classes are large protein complexes formed by association of two separate proteins. Each class includes trans-membrane domains that anchor the complex into the cell membrane. MHC class I molecules are formed from two non-covalently associated proteins, the $\alpha$ chain and $\beta$2-microglobulin. The $\alpha$ chain comprises three distinct domains, $\alpha$1, $\alpha$2 and $\alpha$3. The three dimensional structure of the $\alpha$1 and $\alpha$2 domains forms the groove into which antigens fit for presentation to T-cells. The $\alpha$3 domain is a trans-membrane Ig-fold like domain that anchors the $\alpha$ chain into the cell membrane of the APC. MHC class I complexes, when associated with antigen (and in the presence of appropriate co-stimulatory signals) stimulate CD8 cytotoxic T-cells, which function to kill any cell which they specifically recognize.

The two proteins which associate non-covalently to form MHC class II molecules are termed the $\alpha$ and $\beta$ chains. The $\alpha$ chain comprises $\alpha$1 and $\alpha$2 domains, and the $\beta$ chain comprises $\beta$1 and $\beta$2 domains. The cleft into which the antigen fits is formed by the interaction of the $\alpha$1 and $\beta$1 domains. The $\alpha$2 and $\beta$2 domains are trans-membrane Ig-fold like domains that anchors the $\alpha$ and $\beta$ chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response and to regulate other cells in the immune system.

The genes encoding the various proteins that constitute the MHC complexes have been extensively studied in humans and other mammals. In humans, MHC molecules (with the exception of class I $\beta$2-microglobulin) are encoded in the HLA region, which is located on chromosome 6 and constitutes over 100 genes. There are 3 class I MHC $\alpha$ protein loci, termed HLA-A, -B and -C. There are also 3 pairs of class II MHC $\alpha$ and $\beta$ chain loci, termed HLA-DR(A and B), HLA-DP(A and B), and HLA-DQ(A and B). In rats, the class I $\alpha$ gene is termed RT1.A, while the class II genes are termed RT1.B$\alpha$ and RT1.B$\beta$. More detailed background information on the structure, function and genetics of MHC complexes can be found in *Immunobiology: The Immune System in Health and Disease* by Janeway and Travers, Cuurent Biology Ltd./Garland Publishing, Inc. (1997) (ISBN 0-8153-2818-4), and in Bodmer et al. (1994) "Nomenclature for factors of the HLA system" *Tissue Antigens* vol. 44, pages 1–18 (with periodic updates).

The key role that MHC complexes play in triggering immune recognition has led to the development of methods by which these complexes are used to modulate the immune response. For example, activated T-cells which recognize "self" antigens (autoantigens) are known to play a key role in autoimmune diseases (such as rheumatoid arthritis and multiple sclerosis). Building on the observation that isolated MHC class II molecules (loaded with the appropriate antigen) can substitute for APCs carrying the MHC class II complex and can bind to antigen-specific T-cells, a number of researchers have proposed that isolated MHC/antigen complexes may be used to treat autoimmune disorders. Thus U.S. Pat. No. 5,194,425 (Sharma et al.) and U.S. Pat. No. 5,284,935 (Clark et al.) disclose the use of isolated MHC class II complexes loaded with a specified autoantigen and conjugated to a toxin to eliminate T-cells that are specifically immunoreactive with autoantigens. In another context, it has been shown that the interaction of isolated MHC II/antigen complexes with T-cells, in the absence of co-stimulatory factors, induces a state of non-responsiveness known as anergy. (Quill et al., *J. Immunol.*, 138:3704–3712 (1987)). Following this observation, Sharma et al. (U.S. Pat. Nos. 5,468,481 and 5,130,297) and Clarke et al. (U.S. Pat. No. 5,260,422) have suggested that such isolated MHC II/antigen complexes may be administered therapeutically to anergize T-cell lines which specifically respond to particular autoantigenic peptides.

Methods for using isolated MHC complexes in the detection, quantification and purification of T-cells which recognize particular antigens have been studied for use in diagnostic and therapeutic applications. By way of example, early detection of T-cells specific for a particular autoantigen would facilitate the early selection of appropriate treatment regimes. The ability to purify antigen-specific T-cells would also be of great value in adoptive immunotherapy. Adoptive immunotherapy involves the removal of T-cells from a cancer patient, expansion of the T-cells in vitro and then reintroduction of the cells to the patient (see U.S. Pat. No. 4,690,915; Rosenberg et al. *New Engl. J. Med.* 319:1676–1680 (1988)). Isolation and expansion of cancer specific T-cells with inflammatory properties would increase the specificity and effectiveness of such an approach.

To date, however, attempts to detect, quantify or purify antigen specific T-cells using isolated MvHC/antigen complexes have not met with widespread success because, among other reasons, binding between the T-cells and such isolated complexes is transient and hence the T-cell/MHC/antigen complex is unstable. In an attempt to address these problems, Altman et al. (*Science* 274, 94–96 (1996) and U.S. Pat. No. 5,635,363) have proposed the use of large, covalently linked multimeric structures of MHC/antigen complexes to stabilize this interaction by simultaneously binding to multiple T-cell receptors on a target T-cell.

Although the concept of using isolated MHC/antigen complexes in therapeutic and diagnostic applications holds great promise, a major drawback to the various methods reported to date is that the complexes are large and consequently difficult to produce and to work with. While the complexes can be isolated from lymphocytes by detergent extraction, such procedures are inefficient and yield only small amounts of protein. The cloning of the genes encoding the various MHC complex subunits has facilitated the production of large quantities of the individual subunits through expression in prokaryotic cells, but the assembly of the individual subunits into MHC complexes having the appropriate conformational structure has proven difficult.

SUMMARY OF THE INVENTION

This invention is founded on the discovery that mammalian MHC function can be mimicked through the use of recombinant polypeptides that include only those domains of MHC molecules, that define the antigen binding cleft. These molecules are useful to detect, quantify and purify antigen-specific T-cells. The molecules provided herein may also be used in clinical and laboratory applications to detect, quantify and purify antigen-specific T-cells, induce anergy in T-cells, as well as to stimulate T-cells, and to treat diseases mediated by antigen-specific T-cells.

By way of example, while Altman et al. (U.S. Pat. No. 5,635,363) contemplate the use of multimers of MHC class II complexes comprising α1, α2, β1 and β2 domains and associated peptide antigens, to bind to and purify antigen-specific T-cells from a mixture, the present inventors have discovered that such antigen-specific T-cell binding can be accomplished with a much simpler monomeric molecule comprising, in the case of class II MHC molecules, only the α1 and β1 domains in covalent linkage (and in association with an antigenic determinant). For convenience, such MHC class II polypeptides are hereinafter referred to as "β1α1". Equivalent molecules derived from MHC class I molecules are also provided by this invention. Such molecules comprise the α1 and α2 domains of class I molecules in covalent linkage and in association with an antigenic determinant. Such MHC class I polypeptides are referred to as "α1α2". These two domain molecules may be readily produced by recombinant expression in prokaryotic or eukaryotic cells, and readily purified in large quantities. Moreover, these molecules may easily be loaded with any desired peptide antigen, making production of a repertoire of MHC molecules with different T-cell specificities a simple task.

It is shown that, despite lacking the trans-membrane Ig fold domains that are part of intact MHC molecule, these two domain MHC molecules refold in a manner that is structurally analogous to "whole" MHC molecules, and bind peptide antigens to form stable MHC/antigen complexes. Moreover, these two domain MHC/epitope complexes bind T-cells in an epitope-specific manner, and inhibit epitope-specific T-cell proliferation in vitro. In addition, administration of β1α1 molecules loaded with the myelin basic protein (MBP) epitope comprising amino acids 69–89 of MBP to rats is shown to both suppress the onset of and treat experimental autoimmune encephalomyelitis (EAE) in rats. Thus, the two domain MHC molecules display powerful and epitope-specific effects on T-cell activation both in vitro and in vivo. As a result, the disclosed MHC molecules are useful in a wide range of both in vivo and in vitro applications.

Various formulations of these two domain molecules are provided by the invention. In their most basic form, the two domain MHC class II molecules comprise α1 and β1 domains of a mammalian MHC class II molecule wherein the amino terminus of the α1 domain is covalently linked to the carboxy terminus of the β1 domain and wherein the polypeptide does not include the α2 or β2 domains. The two domain MHC class I molecules comprise an a α1 and α2 domains of a mammalian class I molecule, wherein the amino terminus of the α2 domain is covalently linked to the carboxy terminus of the α1 domain, and wherein the polypeptide does not include an MHC class I α3 domain. For most applications, these molecules are associated, by covalent or non-covalent interaction, with an antigenic determinant, such as a peptide antigen. In certain embodiments, the peptide antigen is covalently linked to the amino terminus of the β1 domain of the class II molecules, or the α1 domain of the class I molecules. The two domain molecules may also comprise a detectable marker, such as a fluorescent label or a toxic moiety, such as ricin A.

The invention also provides nucleic acid molecules that encode the two domain MHC molecules, as well as expression vectors that may be conveniently used to express these molecules. In particular embodiments, the nucleic acid molecules include sequences that encode the antigenic peptide as well as the two domain MHC molecule. For example, one such nucleic acid molecule may be represented by the formula Pr-P-B-A, wherein Pr is a promoter sequence operably linked to P (a sequence encoding the peptide antigen), B is the class I α1 or the class II β1 domain, and A is the class I α2 domain or the class II α1 domain. In these nucleic acid molecules, P, B and A comprise a single open reading frame, such that the peptide and the two MHC domains are expressed as a single polypeptide chain.

In vitro, the two domain MHC molecules may be used to detect and quantify T-cells, and regulate T-celt function. Thus, such molecules loaded with a selected antigen may be used to detect, monitor and quantify the population of a T-cells that are specific for that antigen. The ability to do this is beneficial in a number of clinical settings, such as monitoring the number of tumor antigen-specific T-cells in blood removed from a cancer patient, or the number of self-antigen specific T-cells in blood removed from a patient suffering from an autoimmune disease. In these contexts, the disclosed molecules are powerful tools for monitoring the progress of a particular therapy. In addition to monitoring and quantifying antigen-specific T-cells, the disclosed molecules may also be used to purify such cells for adoptive immunotherapy. Thus, the disclosed MHC molecules loaded with a tumor antigen may be used to purify tumor-antigen specific T-cells from a cancer patient. These cells may then be expanded in vitro before being returned to the patient as part of a cancer treatment. When conjugated with a toxic moiety, the two domain molecules may be used to kill T-cells having a particular antigen specificity. Alternatively, the molecules may also be used to induce anergy in such T-cells.

The two domain molecules may also be used in vivo to target specified antigen-specific T-cells. By way of example, a β1α1 molecule loaded with a portion of myelin basic protein (MBP) and administered to patients suffering from multiple sclerosis may be used to induce anergy in NIBP-specific T-cells, thus alleviating the disease symptoms. Alternatively, such molecules may be conjugated with a toxic moiety to more directly kill the disease-causing T-cells.

These and other aspects of the invention are described in more detail in the following sections.

BRIEF DESCRIPTION OF THE DRAWINGS

FIG. 1A, shows the sequences of the prototypical β1α1 cassette without an antigen coding region. Unique NcoI, PstI, and XhoI restriction sites are in bold. The end of the β1 domain and start of the α1 domain are indicated. FIG. 1B shows the sequence of an in-frame antigenic peptide/linker insertion sequence that can be incorporated into the expression cassette at the insertion site shown (▲) in FIG. 1A. This sequence includes the rat MBP 72–89 antigen, a flexible linker with an embedded thrombin cleavage site, and a unique SpeI restriction site that can be used for facile exchange of the antigen coding region. Example 2 below discusses the use of the equivalent peptide from Guinea pig, which has a serine in place of the threonine residue in the MBP 72–89 sequence. FIGS. 1C and 1D show exemplary Nco1/SpeI fragments that can be inserted into the expression cassette in place of the MBP-72–89 antigen coding region. FIG. 1C includes the MBP 55–69 antigen, FIG. 1D includes the CM-2 antigen.

FIGS. 2A and B show the structure-based design of the β1α1 molecule. A. Rat class II RT1.B, loaded with the encephalitogenic MBP-69–89 peptide. B. The single-chain β1α1 molecule, loaded with MBP-69–89.

FIGS. 3A and B show direct detection of antigen-specific β1α1/polypeptide molecules binding rat T cells. The A1 T cell hybridoma (BV8S2 TCR+) and the CM-2 cell line (BV8S2 TCR−) were incubated 17 hours at 4° C. with various β1α1 constructs, washed, stained for 15 min with OX6-PE (α-RT1.B) or a PE-isotype control and then analyzed by FACS. Background expression of I-A on the CM-2 line was blocked with unlabeled OX-6. A. Histogram showing staining of the A1 hybridoma. B. Histogram showing staining of the CM-2 cell line.

FIG. 4 is a graph showing binding of A488 conjugated β1α1/polypeptide molecules to rat BV8S2 TCR. β1α1 molecules were conjugated with Alexa-488 dye, loaded with MBP-69–89, incubated with the A1 T cell hybridomas (BV8S2 TCR+) for 3 hours at 4° C. and then analyzed by FACS. A488-β1α1 (empty) and A488-β1α1/MBP-69–89, as indicated.

FIG. 5 is a bar graph showing that the β1α1/MBP-69–89 complex blocks antigen specific proliferation in an IL-2 reversible manner. Short-term T cell lines selected with MBP-69–89 peptide from lymph node cells from rats immunized 12 days earlier with Gp-MBP/CFA were pre-treated for 24 hours with β1α1 constructs, washed, and then used in proliferation assays in which the cells were cultured with and without 20 Units/ml IL-2. Cells were incubated for three days, the last 18 hr in the presence of [$^3$H]thymidine (0.5 μCi/10 μl/well). Values indicated are the mean CPM±SEM. Background was 210 CPM. Column a. Control proliferation assay without IL-2. Column b. 20 μM β1α1/MBP-55–69 pretreatment. Column c. 10 nM β1α1/MBP-69–89 pretreatment. Column d. 10 nM β1α1/MBP-69–89 plus IL-2 during the proliferation assay. A single representative experiment is shown; the experiment was done twice. *indicates significant (p<0.001) inhibition with β1α1/MBP-69–89 versus control cultures.

FIGS. 6A–D are graphs showing clinical protection from experimental autoimmune encephalomyelitis with the β1α1/MBP-69–89 complex. Groups of Lewis rats (n=6) were injected with 25 μg of Gp-MBP/CFA to induce clinical EAE. On days 3, 7, 9, 11, and 14 after disease induction rats were given β1α1/peptide complex, peptide alone, or were left untreated, as indicated. A. No treatment, or 2 μg MBP-69–89 peptide alone, as indicated. B. 300 μg of β1α1/(empty) complex in saline. C. 300 μg of β1α1/CM-2 complex in saline. D. 30 μg of β1α1/MBP-69-89 complex in saline. Daily body weight (grams, right-hand y-axis) is plotted for the 300 μg β1α1/peptide complex treatments. A single representative experiment is shown; the experiment was done three times. Values indicate mean clinical score ±SEM on each day of clinical disease. 30 μg of complex is equivalent to 2 μg of free peptide.

FIG. 7 is a graph showing treatment of established EAE with β1α1/MBP-69–89 complex. Groups of Lewis rats (n=6) were injected with 25 μg of Gp-MBP/CFA to induce clinical EAE. On the day of onset of clinical signs (day 11), day 13, and day 15, rats were given 300 μg of β1α1/MBP-69–89 complex (indicated by arrows) or were left untreated. A single representative experiment is shown; the experiment was done twice. Values indicate mean clinical score ±SEM on each day of clinical disease.

FIGS. 8A and B are graphs showing that the β1α1/MBP-69–89 complex specifically inhibits the DTH response to MBP 69–89. A. Change in ear thickness 24 hrs after challenge with PPD. B. Change in ear thickness 24 hrs after challenge with MBP-69-89. Values indicate mean score ±SEM. *Indicates significant difference between control and treated (p=0.01). A single representative experiment is shown; the experiment was done twice.

FIG. 9 is a graph showing that T cell responses to MBP-69–89 were inhibited in Lewis rats treated with 300 μg β1α1/MBP-69–89 complex. Lymph node cells were collected from control and treated rats after recovery of controls from EAE (day 17) and stimulated with optimal concentrations of Gp-MBP, Gp-MBP-69–89 peptide, or PPD. *Indicates significant difference between control and treated (*p<0.05; **p<0.001). Note inhibition with Gp MBP and DABP-69–89 peptide but not to PPD in treated rats.

FIGS. 10A–C shows the amino acid sequences of exemplary (A) human (DRA and DRB1 0101), (B) mouse (I-EK) and (C) rat (RT1.B) β1 and α1 domains (the initiating methione and glycine sequences in the rat sequence were included in a construct for translation initiation reasons).

FIG. 11 shows the amino acid sequences of exemplary α1 and α2 domains derived from human MHC class I B*5301.

Sequence Listing

The sequence listing appended hereto includes sequences as follows:

- Seq. I.D. No. 1: the nucleic acid of a single chain β1α1 expression cassette.
- Seq. I.D. No. 2: the amino acid sequence encoded by the construct shown in Seq. I.D. No. 1.
- Seq. I.D. No. 3: the nucleic acid sequence of an antigen/linker insert suitable for insertion into the expression cassette shown in Seq. I.D. No. 1.
- Seq. I.D. No. 4: the amino acid sequence encoded by the sequence shown in Seq. I.D. No. 3.
- Seq. I.D. Nos. 5 and 7: alternative antigen encoding sequences for the expression cassette and, Seq. I.D. Nos. 6 and 8, the antigen sequences encoded by the sequences shown in Seq. I.D. Nos. 5 and 7, respectively.
- Seq. I.D. Nos. 9–20 and 28–29 show PCR primers use to amplify components of the β1α1 expression cassette.
- Seq. ID. No. 21 shows the exemplary α1 and α2 domains depicted in FIG. 11.
- Seq. I.D. Nos. 22–24 show the exemplary β1 and α1 domains depicted in FIG.
- Seq. I.D. Nos. 25–27 and 30 show peptides sequences used in various aspects of the invention.

DETAILED DESCRIPTION OF THE INVENTION

1. Definitions

Figure 3:
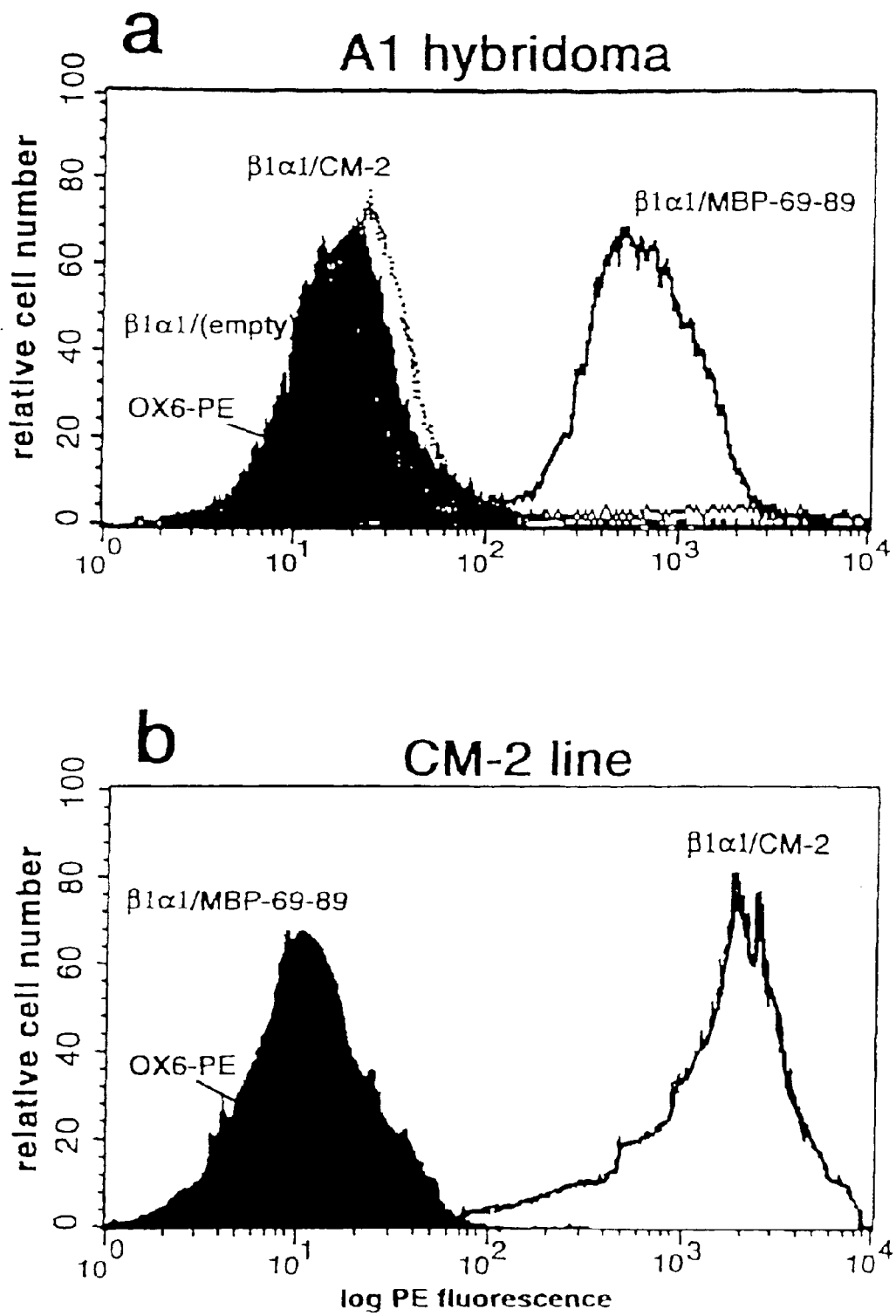

In order to facilitate review of the various embodiments of the invention, the following definitions of terms and explanations of abbreviations are provided:

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

cDNA (complementary DNA): a piece of DNA lacking internal, non-coding segments (introns) and regulatory sequences which determine transcription. cDNA is synthesized in the laboratory by reverse transcription from messenger RNA extracted from cells.

ORF (open reading frame): a series of nucleotide triplets (codons) coding for amino acids without any termination codons. These sequences are usually translatable into a polypeptide.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990. PCR primer pairs can be derived from a known sequence, for example, by using computer programs intended for that purpose such as Primer (Version 0.5, © 1991, Whitehead Institute for Biomedical Research, Cambridge, Mass.).

Purified: the term purified does not require absolute purity; rather, it is intended as a relative term. Thus, for example, a purified recombinant MHC protein preparation is one in which the recombinant MHC protein is more pure than the protein in its originating environment within a cell. A preparation of a recombinant MHC protein is typically purified such that the recombinant MHC protein represents at least 50% of the total protein content of the preparation. However, more highly purified preparations may be required for certain applications. For example, for such applications, preparations in which the MHC protein comprises at least 75% or at least 90% of the total protein content may be employed.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Mammal: This term includes both human and non-human mammals. Similarly, the term "patient" includes both human and veterinary subjects.

$\beta 1 \alpha 1$ polypeptide: a recombinant polypeptide comprising the $\alpha 1$ and $\beta 1$ domains of a MHC class II molecule in covalent linkage. To ensure appropriate conformation, the orientation of such a polypeptide is such that the carboxy terminus of the $\oplus 1$ domain is covalently linked to the amino terminus of the $\alpha 1$ domain.

$\beta 1 \alpha 1$ gene: a recombinant nucleic acid sequence including a promoter region operably linked to a nucleic acid sequence encoding a $\beta 1 \alpha 1$ polypeptide.

$\beta 1 \alpha 2$ polypeptide: a polypeptide comprising the $\alpha 1$ and $\alpha 2$ domains of a MHC class I molecule in covalent linkage. The orientation of such a polypeptide is such that the carboxy terminus of the $\alpha 1$ domain is covalently linked to the amino terminus of the $\alpha 2$ domain. An $\alpha 1$ $\alpha 2$ polypeptide comprises less than the whole class I $\alpha$ chain, and usually omits most or all of the $\alpha 3$ domain of the $\alpha$ chain.

$\alpha 1 \alpha 2$ gene: a recombinant nucleic acid sequence including a promoter region operably linked to a nucleic acid sequence encoding an $\alpha 1 \alpha 2$ polypeptide.

Domain: a domain of a polypeptide or protein is a discrete part of an amino acid sequence that can be equated with a particular function. For example, the $\alpha$ and $\beta$ polypeptides that constitute a MHC class II molecule are each recognized as having two domains, $\alpha 1$, $\alpha 2$ and $\beta 1$, $\beta 2$, respectively. Similarly, the $\alpha$ chain of MHC class I molecules is recognized as having three domains, $\alpha 1$, $\alpha 2$ and $\alpha 3$. The various domains in each of these molecules are typically joined by linking amino acid sequences. When selecting the sequence of a particular domain for inclusion in a recombinant molecule, it is preferable that the entire domain be included; to ensure that this is done, the domain sequence may be extended to include part of the linker, or even part of the adjacent domain. For example, when selecting the $\alpha 1$ domain of HLA-DR A, the selected sequence will generally extend from amino acid residue number 1 of the $\alpha$ chain, through the entire $\alpha 1$ domain and will include include all or part of the linker sequence located at about amino acid residues 76–90 (at the carboxy terminus of the $\alpha 1$ domain, between the $\alpha 1$ and $\alpha 2$ domains). However, the precise number of amino acids in the various MHC molecule domains varies depending on the species of mammal, as well as between classes of genes within a species. Rather than a precise structural definition based on the number of amino acids, it is the maintenance of domain function that is important when selecting the amino acid sequence of a particular domain. Moreover, one of skill in the art will appreciate that domain function may also be maintained if somewhat less than the entire amino acid sequence of the selected domain is utilized. For example, a number of amino acids at either the amino or carboxy terminii of the $\alpha 1$ domain may be omitted without affecting domain function. Typically however, the number of amino acids omitted from either terminus of the domain sequence will be no greater than 10, and more typically no greater than 5. The functional activity of a particular selected domain may be assessed in the context of the two-domain MHC polypeptides provided by this invention (i.e., the class II β1α1 or class I α1α2 polypeptides) using the antigen-specific T-cell proliferation assay as described in detail below. For example, to test a particular β1 domain, it will be linked to a functional α1 domain so as to produce β1α1 molecule and then tested in the described assay. A biologically active β1α1 or α1α2 polypeptide will inhibit antigen-specific T cell proliferation by at least about 50%, thus indicating that the component domains are functional. Typically, such polypeptides will inhibit T-cell proliferation in this assay system by at least 75% and sometimes by greater than about 90%.

Sequence identity: the similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of MHC domain polypeptides will possess a relatively high degree of sequence identity when aligned using standard methods. (An "MHC domain polypeptide" refers to an α1 or β1 domain of an MHC class II polypeptide or an α1 or α2 domain of an MHC class I polypeptide).

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at htp://www.ncbi.nlm.nih.gov/BLAST/. A description of how to determine sequence identity using this program is available at http://www.ncbi.nlm.nih.gov/BLAST/blast_help.html.

Variants of MHC domain polypeptides are typically characterized by possession of at least 50% sequence identity counted over the full length alignment with the amino acid sequence of a native MHC domain polypeptide using the NCBI Blast 2.0, gapped blastp set to default parameters. Proteins with even greater similarity to the reference sequences will show increasing percentage identities when assessed by this method, such as at least 60%, at least 65%, at least 7,0%, at least 75%, at least 80%, at least 90% or at least 95% sequence identity. When less than the entire sequence is being compared for sequence identity, variants will typically possess at least 75% sequence identity over short windows of 10–20 amino acids, and may possess sequence identities of at least 85% or at least 90% or 95% depending on their similarity to the reference sequence. Methods for determining sequence identity over such short windows are described at http://www.ncbi.nlm.nih.gov/BLAST/blast_FAOs.html. Variants of MHC domain polypeptides also retain the biological activity of the native polypeptide. For the purposes of this invention, that activity is conveniently assessed by incorporating the variant domain in the appropriate β1α1 or α1α2 polypeptide and determining the ability of the resulting polypeptide to inhibit antigen specific T-cell proliferation in vitro, as described in detail below.

Linker sequence: a linker sequence is an amino acid sequence that covalently links two polypeptide domains. Linker sequences may be included in the recombinant MHC polypeptides of the present invention to provide rotational freedom to the linked polypeptide domains and thereby to promote proper domain folding and inter- and intra-domain bonding. By way of example, in a recombinant polypeptide comprising Ag-β1-α1 (where Ag=antigen) linker sequences may be provided between both the Ag and β1 domains and between β1 and α1 domains. Linker sequences, which are generally between 2 and 25 amino acids in length, are well known in the art and include the glycine(4)-serine spacer (GGGGS×3) described by Chaudhary et al. (1989).

Recombinant MHC class I α1α2 polypeptides according to the present invention include a covalent linkage joining the carboxy terminus of the α1 domain to the amino terminus of the α2 domain. The α1 and α2 domains of native MHC class I α chains are typically covalently linked in this orientation by an amino acid linker sequence. This native linker sequence may be maintained in the recombinant constructs; alternatively, a recombinant linker sequence may be introduced between the α1 and α2 domains (either in place of or in addition to the native linker sequence).

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The following sections provide detailed guidance on the design, expression and uses of the recombinant MHC molecules of the invention. Unless otherwise stated, standard molecular biology, biochemistry and immunology methods are used in the present invention unless otherwise described. Such standard methods are described in Sambrook et al. (1989), Ausubel et al (1987), Innis et al. (1990) and Harlow and Lane (1988). The following U.S. patents which relate to conventional formulations of MHC molecules and their uses are incorporated herein by reference to provide additional background and technical information relevant to the present invention: U.S. Pat Nos. 5,130,297; 5,194,425; 5,260,422; 5,284,935; 5,468,481; 5,595,881; 5,635,363; 5,734,023.

2. Design Of Recombinant MHC Class II β1α1 Molecules

The amino acid sequences of mammalian MHC class II α and β chain proteins, as well as nucleic acids encoding these proteins, are well known in the art and available from numerous sources including GenBank. Exemplary sequences are provided in Auffray et al. (1984) (human HLA DQ α); Larhammar et al. (1983) (human HLA DQ β); Das et al. (1983) (human HLA DR α); Tonnelle et al. (1985) (human HLA DR β); Lawrance et al. (1985) (human HLA DP α); Kelly et al. (1985) (human HLA DP β); Syha et al. (1989) (rat RT1.B α); Syha-Jedelhauser et al. (1991) (rat RT1B.β); Benoist et al. (1983) (mouse I-A α); Estess et al. (1986) (mouse I-A β).

The recombinant MHC class II molecules of the present invention comprise the β1 domain of the MHC class II β chain covalently linked to the α1 domain of the MHC class II α chain. The β1 and α1 domains are well defined in mammalian MHC class II proteins. Typically, the α1 domain is regarded as comprising about residues 1–90 of the mature α chain. The native peptide linker region between the α1 and α2 domains of the MHC class II protein spans from about amino acid 76 to about amino acid 93 of the α chain, depending on the particular α chain under consideration. Thus, an α1 domain may include about amino acid residues 1–90 of the α chain, but one of skill in the art will recognize that the C-terminal cut-off of this domain is not necessarily precisely defined, and, for example, might occur at any point between amino acid residues 70–100 of the α chain. The composition of the α1 domain may also vary outside of these parameters depending on the mammalian species and the particular α chain in question. One of skill in the art will appreciate that the precise numerical parameters of the amino acid sequence are much less important than the maintenance of domain function.

Similarly, the β1 domain is typically regarded as comprising about residues 1–90 of the mature β chain. The linker region between the β1 and β2 domains of the MHC class II protein spans from about amino acid 85 to about amino acid 100 of the β chain, depending on the particular β chain under consideration. Thus, the β1 protein may include about amino acid residues 1–100, but one of skill in the art will again recognize that the C-terminal cut-off of this domain is not necessarily precisely defined, and, for example, might occur at any point between amino acid residues 75–105 of the β chain. The composition of the β1 domain may also vary outside of these parameters depending on the mammalian species and the particular β chain in question. Again, one of skill in the art will appreciate that the precise numerical parameters of the amino acid sequence are much less important than the maintenance of domain function. Exemplary β1α1 molecules from human, rat and mouse are depicted in FIG. 10.

Nucleic acid molecules encoding these domains may be produced by standard means, such as amplification by the polymerase chain reaction (PCR). Standard approaches for designing primers for amplifying open reading frames encoding these domain may be employed. Libraries suitable for the amplification of these domains include, for example, cDNA libraries prepared from the mammalian species in question; such libraries are available commercially, or may be prepared by standard methods. Thus, for example, constructs encoding the β1 and α1 polypeptides may be produced by PCR using four primers: primers B1 and B2 corresponding to the 5' and 3' ends of the β1 coding region, and primers A1 and A2 corresponding to the 5' and 3' ends of the α1 coding region. Following PCR amplification of the α1 and β1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, i.e., to maintain the open reading frame. Where the amplified coding regions are separately cloned., the fragments may be subsequently released from the cloning vector and gel purified, preparatory to ligation.

In certain embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

3. Design Of Recombinant MHC Class I α1α2 Molecules

The amino acid sequences of mammalian MHC class I α chain proteins, as well as nucleic acids encoding these proteins, are well known in the art and available from numerous sources including GenBank. Exemplary sequences are provided in Browning et al. (1995) (human HLA-A); Kato et al. (1993) (human HLA-B); Steinle et al. (1992) (human HLA-C); Walter et al. (1995) (rat Ia); Walter et al. (1994) (rat Ib); Kress et al. (1983) (mouse H-2-K); Schepart et al. (1986) (mouse H-2-D); and Moore et al. (1982) (mouse H-2-1).

The recombinant MHC class I molecules of the present invention comprise the α1 domain of the MHC class I α chain covalently linked to the α2 domain of the MHC class I α chain. These two domains are well defined in mammalian MHC class I proteins. Typically, the α1 domain is regarded as comprising about residues 1–90 of the mature α chain and the α2 chain as comprising about amino acid residues 90–180, although again, the cut-off points are not precisely defined and will vary between different MHC class I molecules. The boundary between the α2 and α3 domains of the MHC class I α protein typically occurs in the region of amino acids 179–183 of the mature α chain. The composition of the α1 and α2 domains may also vary outside of these parameters depending on the mammalian species and the particular α chain in question. One of skill in the art will appreciate that the precise numerical parameters of the amino acid sequence are much less important than the maintenance of domain function. An exemplary α1α2 molecule is depicted in FIG. 11.

The α1α2 construct may be most conveniently constructed by amplifying the reading frame encoding the dual-domain (α1 and α2) region between amino acid number 1 and amino acids 179–183, although one of skill in the art will appreciate that some variation in these end-points is possible. Such a molecule includes the native linker region between the α1 and α2 domains, but if desired that linker region may be removed and replaced with a synthetic linker peptide. The general considerations for amplifying and cloning the MHC class I α1 and α2 domains apply as discussed above in the context of the class II β1 and α1 domains.

4. Genetic Linkage of of Antigenic Polypeptide to β1α1 and α1α2 Molecules The class II β1αand class I α1α2 polypeptides of the invention are generally used in conjunction with an antigenic peptide. Any antigenic peptide that is conventionally associated with class I or class II MHC molecules and recognized by a T-cell can be used for this purpose. Antigenic peptides from a number of sources have been characterized in detail, including antigenic peptides from honey bee venom allergens, dust mite allergens, toxins produced by bacteria (such as tetanus toxin) and human tissue antigens involved in autoimmune diseases. Detailed discussions of such peptides are presented in U.S. Pat. Nos. 5,595,881, 5,468,481 and 5,284,935. Exemplary peptides include those identified in the pathogenesis of rheumatoid arthritis (type II collagen), myasthenia gravis (acetyl choline receptor), and multiple sclerosis (myelin basic protein).

As is well known in the art (see for example U.S. Pat. No. 5,468,481) the presentation of antigen in MHC complexes on the surface of APCs generally does not involve a whole antigenic peptide. Rather, a peptide located in the groove between the β1 and α1 domains (in the case of MHC II) or the α1 and α2 domains (in the case of MHC I) is typically a small fragment of the whole antigenic peptide. As discussed in Janeway & Travers (1997), peptides located in the peptide groove of MHC class I molecules are constrained by the size of the binding pocket and are typically 8–15 amino acids long, more typically 8–10 amino acids in length (but see Collins et al., 1994 for possible exceptions). In contrast, peptides located in the peptide groove of MHC class II molecules are not constrained in this way and are often much larger, typically at least 13 amino acids in length. Peptide fragments for loading into MHC molecules can be prepared by standard means, such as use of synthetic peptide synthesis machines.

The β1α1 and α1α2 molecules of the present invention may be "loaded" with peptide antigen in a number of ways, including by covalent attachment of the peptide to the MHC molecule. This may be conveniently achieved by operably linking a nucleic acid sequence encoding the selected peptide to the 5' end of the construct encoding the MHC protein such that, in the expressed peptide, the antigenic peptide domain is linked to the N-terminus of β1 in the case of β1α1 molecules and α1 in the case of α1α2 molecules. One convenient way of obtaining this result is to incorporate a sequence encoding the antigen into the PCR primers used to amplify the MHC coding regions. Typically, a sequence encoding a linker peptide sequence will be included between the molecules encoding the antigenic peptide and the MHC polypeptide. As discussed above, the purpose of such linker peptides is to provide flexibility and permit proper conformational folding of the peptides. For linking antigens to the MHC polypeptide, the linker should be sufficiently long to permit the antigen to fit into the peptide groove of the MHC polypeptide. Again, this linker may be conveniently incorporated into the PCR primers. However, as discussed in Example 1 below, it is not necessary that the antigenic peptide be ligated exactly at the 5' end of the MHC coding region. For example, the antigenic coding region may be inserted within the first few (typically within the first 10) codons of the 5' end of the MHC coding sequence.

This genetic system for linkage of the antigenic peptide to the MHC molecule is particularly useful where a number of MHC molecules with differing antigenic peptides are to be produced. The described system permits the construction of an expression vector in which a unique restriction site is included at the 5' end of the MHC coding region (i.e., at the 5' end of β1 in the case of β1α1-encoding constructs and at the 5' end of α1 in the case of α1α2-encoding constructs). In conjunction with such a construct, a library of antigenic peptide-encoding sequences is made, with each antigen-coding region flanked by sites for the selected restriction enzyme. The inclusion of a particular antigen into the MHC molecule is then performed simply by (a) releasing the antigen-coding region with the selected restriction enzyme, (b) cleaving the MHC construct with the same restriction enzyme, and (c) ligating the antigen coding region into the MHC construct. In this manner, a large number of MHC-polypeptide constructs can be made and expressed in a short period of time.

An exemplary design of an expression cassette allowing simple exchange of antigenic peptides in the context of a β1α1 molecule is shown in FIG. 1. FIG. 1A shows the nucleic acid sequence encoding a prototype β1α1 molecule derived from rat MHC class II RT1.B, without the presence of the antigenic peptide. The position of the insertion site for the peptide and linker between the 5th and 6th (serine and proline) residues of the β1 domain is indicated by a ▲symbol. In order to integrate the antigen coding region, a PCR primer comprising the sequence shown in FIG. 1B joined with additional bases from the FIG. 1A construct 3' of the insertion site is employed in conjunction with a PCR primer reading from the 3' end of the construct shown in FIG. 1A.) Amplification yields a product that includes the sequence shown in FIG. 1B integrated into the β1α1 construct (i.e., with the antigenic peptide and linker sequences positioned between the codons encoding the 5th and 6th amino acid residues of the β1α1 sequence). In the case illustrated, the antigenic peptide is the MBP-72–89 antigen.

Notably, the MBP-72–89 coding sequence is flanked by unique Nco I and Spe I restriction enzyme sites. These enzymes can be used to release the MBP-72–89 coding region and replace it with coding regions for other antigens, for example those illustrated in FIGS. 1C and 1D.

The structure of the expressed β1α1 polypeptide with covalently attached antigen is illustrated in FIG. 2B; FIG. 2A shows the secondary structure of the complete RT1B molecule (including α1, α2, β1 and β2 domains).

Nucleic acid expression vectors including expression cassettes designed as explained above will be particularly useful for research purposes. Such vectors will typically include sequences encoding the dual domain MHC polypeptide (β1α1 or α1α2) with a unique restriction site provided towards the 5' terminus of the MHC coding region, such that a sequence encoding an antigenic polypeptide may be conveniently attached. Such vectors will also typically include a promoter operably linked to the 5' terminus of the MHC coding region to provide for high level expression of the sequences.

β1α1 and α1α2 molecules may also be expressed and purified without an attached peptide (as described in section 5 below), in which case they may be referred to as "empty". The empty MHC molecules may then be loaded with the selected peptide as described in section 6 below.

5. Expression and Purification of Recombinant β1α1 and α1α2 Molecules

In their most basic form, nucleic acids encoding the MHC polypeptides of the invention comprise first and second regions, having a structure A–B wherein, for class I molecules, region A encodes the class I α1 domain and region B encodes the class I α2 domain. For class II molecules, A encodes the class II β1 domain and B encodes the class II α1 domain. Where a linker sequence is included, the nucleic acid may be represented as B-L2-A, wherein L2 is a nucleic acid sequence encoding the linker peptide. Where an antigenic peptide is covalently linked to the MHC polypeptide, the nucleic acid molecule encoding this complex may be represented as P-B-A. A second linker sequence may be provided between the antigenic protein and the region B polypeptide, such that the coding sequence is represented as P-L2-B-L1-A. In all instances, the various nucleic acid sequences that comprise the MHC polypeptide (i.e., L1, L2, B, A and P) are operably linked such that the elements are situated in a single reading frame.

Nucleic acid constructs expressing these MHC polypeptides may also include regulatory elements such as promoters (Pr), enhancers and 3' regulatory regions, the selection of which will be determined based upon the type of cell in which the protein is to be expressed. When a promoter sequence is operably linked to the open reading frame, the sequence may be represented as Pr-B-A, or (if an antigen-coding region is included) Pr-P-B-A, wherein Pr represents the promoter sequence. The promoter sequence is operably linked to the P or B components of these sequences, and the B-A or P-B-A sequences comprise a single open reading frame. The constructs are introduced into a vector suitable for expressing the MHC polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), 'phage T7 and lambda $P_L$ promoters. Methods and plasmid vectors for producing heterologous proteins in bacteria are described in Sambrook et al. (1989). Suitable prokaryotic cells for expression of large amounts of $\beta_2$m fusion proteins include *Escherichia coli* and *Bacillus subtilis*. Often, proteins expressed at high levels are found in insoluble inclusion bodies; methods for extracting proteins from these aggregates are described by Sambrook et al. (1989) (ch. 17). Recombinant expression of MHC polypeptides in prokaryotic cells may alternatively be conveniently obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli*. and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The MHC polypeptides can also be expressed in eukaryotic expression systems, including *Pichia pastoris*, Drosophila, Baculovirus and Sindbis expression systems produced by Invitrogen (Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express the MHC polypeptides. Regulatory regions suitable for use in these cells include, for mammalian cells, viral promoters such as those from CMV, adenovirus and SV40, and for yeast cells, the promoter for 3-phosphoglycerate kinase and alcohol dehydrogenase.

The transfer of DNA into eukaryotic, in particular human or other mammalian cells, is now a conventional technique. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

An MHC polypeptide produced in mammalian cells may be extracted following release of the protein into the supernatant and may be purified using an immunoaffinity column prepared using anti-MHC antibodies. Alternatively, the MHC polypeptide may be expressed as a chimeric protein with, for example, b-globin. Antibody to b-globin is thereafter used to purify the chimeric protein. Corresponding protease cleavage sites engineered between the b-globin gene and the nucleic acid sequence encoding the MHC polypeptide are then used to separate the two polypeptide fragments from one another after translation. One useful expression vector for generating b-globin chimeric proteins is pSG5 (Stratagene, La Jolla, Calif.).

Expression of the MHC polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells.

Purification of the expressed protein is generally performed in a basic solution (typically around pH 10) containing 6M urea. Folding of the purified protein is then achieved by dialysis against a buffered solution at neutral pH (typically phosphate buffered saline (PBS) at around pH 7.4).

6. Antigen Loading of Empty $\beta 1\alpha 1$ and $\alpha 1\alpha 2$ Molecules

Where the $\beta 1\alpha 1$ and I $\alpha 1\alpha 2$ molecules are expressed and purified in an empty form (i.e., without attached antigenic peptide), the antigenic peptide may be loaded into the molecules using standard methods. Methods for loading of antigenic peptides into MHC molecules is described in, for example, U.S. Pat. No. 5,468,481. Such methods include simple co-incubation of the purified MHC molecule with a purified preparation of the antigen.

By way of example, empty $\beta 1\alpha 1$ molecules (1 mg/ml; 40 uM) may be loaded by incubation with a 10-fold molar excess of peptide (1 mg/ml; 400 uM) at room temperature, for 24 hours. Thereafter, excess unbound peptide may be removed by dialysis against PBS at 4° C. for 24 hours. As is known in the art, peptide binding to $\beta 1\alpha 1$ can be quantified by silica gel thin layer chromatography (TLC) using radiolabeled peptide. Based on such quantification, the loading may be altered (e.g., by changing the molar excess of peptide or the time of incubation) to obtain the desired result.

7. Other Considerations a. Sequence Variants

While the foregoing discussion uses as examples naturally occurring MHC class I and class II molecules and the various domains of these molecules, one of skill in the art will appreciate that variants of these molecules and domains may be made and utilized in the same manner as described. Thus, reference herein to a domain of an MHC polypeptide or molecule (e.g., an MHC class II β1 domain) includes both naturally occurring forms of the referenced molecule, as well as molecules that are based on the amino acid sequence of the naturally occurring form, but which include one or more amino acid sequence variations. Such variant polypeptides may also be defined in the degree of amino acid sequence identity that they share with the naturally occurring molecule. Typically, MHC domain variants will share at least 80% sequence identity with the sequence of the naturally occurring MHC domain. More highly conserved variants will share at least 90% or at least 95% sequence identity with the naturally occurring sequence. Variants of MHC domain polypeptides also retain the biological activity of the naturally occurring polypeptide. For the purposes of this invention, that activity is conveniently assessed by incorporating the variant domain in the appropriate $\beta 1\alpha 1$ or $\alpha 1\alpha 2$ polypeptide and determining the ability of the resulting polypeptide to inhibit antigen specific T-cell proliferation in vitro, as described in detail below.

Variant MHC domain polypeptides include proteins that differ in amino acid sequence from the naturally occurring MHC polypeptide sequence but which retain the specified biological activity. Such proteins may be produced by manipulating the nucleotide sequence of the molecule encoding the domain, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 1 shows amino acids which may be substituted for an original amino acid in a protein and which are regarded as conservative substitutions.

TABLE 1

| Original Residue | Conservative Substitutions |
| --- | --- |
| Ala | ser |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in biological function or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the described T-cell proliferation assay.

At the nucleic acid level, one of skill in the art will appreciate that the naturally occurring nucleic acid sequences that encode class I and II MHC domains may be employed in the expression vectors, but that the invention is not limited to such sequences. Any sequence that encodes a functional MHC domain may be employed, and the nucleic acid sequence may be adapted to conform with the codon usage bias of the organism in which the sequence is to be expressed.

b. Incorporation of Detectable Markers

For certain in vivo and in vitro applications, the MHC molecules of the present invention may be conjugated with a detectable label. A wide range of detectable labels are known, including radionuclides (e.g., gamma-emitting sources such as indium-111), paramagnetic isotopes, fluorescent markers (e.g., fluorescein), enzymes (such as alkaline phosphatase), cofactors, chemiluminescent compounds and bioluminescent compounds. The binding of such labels to the MHC polypeptides may be achieved using standard methods. U.S. Pat. No. 5,734,023 contains an extensive discussion of the labeling of MHC polypeptide derivatives using such labels. Where the detectable marker is to be covalently linked to the MHC molecule in a directed manner (i.e., rather than being randomly attached) it will generally be linked to the C terminus of the molecule so as to minimize interference with a peptide antigen linked at the N terminus.

c. Conjugation of Toxic Moieties

For certain uses of the disclosed MHC polypeptides, particularly in vivo therapeutic applications aimed at depleting certain T-cell populations, the polypeptides may be conjugated with a toxic moiety. Numerous toxic moieties suitable for disrupting T-cell function are known, including protein toxins, chemotherapeutic agents, antibodies to a cytotoxic T-cell surface molecule, lipases, and radioisotopes emitting "hard" e.g., beta radiation. Examples of such toxins and methods of conjugating toxins to MHC molecules are described in U.S. Pat. No. 5,284,935. Protein toxins include ricin, diphtheria and, Pseudomonas toxin. Chemotherapeutic agents include doxorubicin, daunorubicin, methotrexate, cytotoxin, and antisense RNA. Radioisotopes such as yttrium-90, phosphorus-32, lead-212, iodine-131, or palladium-109 may also be used. Where the toxic moiety is to be covalently linked to the MHC molecule in a directed manner (i.e., rather than being randomly attached) it will generally be linked to the C terminus of the molecule so as to minimize interference with a peptide antigen linked at the N terminus.

d. Pharmaceutical Formulations

For administration to animals, purified MHC polypeptides of the present invention are generally combined with a pharmaceutically acceptable carrier. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals may be only inefficiently delivered through ingestion. However, pill-based forms of pharmaceutical proteins may alternatively be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery. Additional possible methods of delivery include deep lung delivery by inhalation (Edwards et al., 1997; Service, 1997) and trans-dermal delivery (Mitragotri et al., 1996).

It is also contemplated that the MHC polypeptides of the present invention could be delivered to cells in the nucleic acid form and subsequently translated by the host cell. This could be done, for example through the use viral vectors or liposomes. Liposomes could also be used for direct delivery of the polypeptides.

The pharmaceutical compositions of the present invention may be administered by any means that achieve their intended purpose. Amounts and regimens for the administration of the selected MHC polypeptides will be determined by the attending clinician. Effective doses for therapeutic application will vary depending on the nature and severity of the condition to be treated, the particular MHC polypeptide selected, the age and condition of the patient and other clinical factors. Typically, the dose range will be from about 0.1 ug/kg body weight to about 100 mg/kg body weight. Other suitable ranges include doses of from about 100 ug/kg to 1 mg/kg body weight. The dosing schedule may vary from once a week to daily depending on a number of clinical factors, such as the subject's sensitivity to the protein. Examples of dosing schedules are 3 ug/kg administered twice a week, three times a week or daily; a dose of 7 ug/kg twice a week, three times a week or daily; a dose of 10 ug/kg twice a week, three times a week or daily; or a dose of 30 ug/kg twice a week, three times a week or daily.

8. Exemplary Applications of Recombinant $\beta 1\alpha 1$ and $\alpha 1\alpha 2$ Molecules The class II $\beta 1\alpha 1$ and class I $\alpha 1\alpha 2$ polypeptides of the present invention are useful for a wide range of in vitro and in vivo applications,. Indeed, as a result of the biological activities of these polypeptides, they may be used in numerous application in place of either intact purified MHC molecules, or antigen presenting cells that express MHC molecules.

In vitro applications of the disclosed polypeptides include the detection, quantification and purification of antigen-specific T-cells. Methods for using various forms of MHC-derived complexes for these purposes are well known and are described in, for example, U.S. Pat. Nos. 5,635,363 and 5,595,881. For such applications, the disclosed polypeptides may be free in solution or may be attached to a solid support such as the surface of a plastic dish, a microtiter plate, a membrane, or beads. Typically, such surfaces are plastic, nylon or nitrocellulose. Polypeptides in free solution are useful for applications such as fluorescence activated sell sorting (FACS). For detection and quantification of antigen-specific T-cells, the polypeptides are preferably labeled with a detectable marker, such as a fluorescent marker.

The T-cells to be detected, quantified or otherwise manipulated are generally present in a biological sample removed from a patient. The biological sample is typically blood or lymph, but may also be tissue samples such as lymph nodes, tumors, joints etc. It will be appreciated that the precise details of the method used to manipulate the T-cells in the sample will depend on the type of manipulation to be performed and the physical form of both the biological sample and the MHC molecules. However, in general terms, the $\beta 1\alpha 1$/peptide complex or $\alpha 1\alpha 2$/peptide complex is added to the biological sample, and the mixture is incubated for sufficient time (e.g., from about 5 minutes up to several hours) to allow binding. Detection and quantification of T-cells bound to the MHC/peptide complex may be performed by a number of methods including, where the MHC/peptide includes a fluorescent label, fluorescence microscopy and FACS. Standard immunoassays such as ELISA and RIA may also be used to quantify T-cell—MHC/peptide complexes where the MHC/peptide complexes are bound to a solid support. Quantification of antigen-specific T-cell populations will be especially useful in monitoring the course of a disease. For example, in a multiple sclerosis patient, the efficacy of a therapy administered to reduce the number of MBP-reactive T-cells may be monitored using MHC/MBP antigen complexes to quantify the number of such T-cells present in the patient. Similarly, the number of anti-tumor T-cells in a cancer patient may be quantified and tracked over the course of a therapy using MHC/tumor antigen complexes.

FACS may also be used to separate T-cell—MHC/peptide complexes from the biological sample, which may be particularly useful where a specified population of antigen-specific T-cells is to be removed from the sample, such as for enrichment purposes. Where the MHC/peptide complex is bound to magnetic beads, the binding T-cell population may be purified as described by Miltenyi et al (1990). By way of example, anti-tumor T-cells in the blood of a cancer patient may be purified using these methods, expanded in vitro and returned to the patient as part of an adoptive immunotherapy treatment.

A specified antigen-specific T-cell population in the biological sample may be anergized by incubation of the sample with MHC/peptide complexes containing the peptide recognized by the targeted T-cells. Thus, when these complexes bind to the TCR in the absence of other co-stimulatory molecules, a state of anergy is induced in the T-cell. Such an approach is useful in situations where the targeted T-cell population recognizes a self-antigen, such as in various autoimmune diseases. Alternatively, the targeted T-cell population may be killed directly by incubation of the biological sample with an MHC/peptide complex conjugated with a toxic moiety.

T-cells may also be activated in an antigen-specific manner by the polypeptides of the invention. For example, the disclosed MHC polypeptides loaded with a specified antigen may be adhered at a high density to a solid surface, such as a plastic dish or a magnetic bead. Exposure of T-cells to the polypeptides on the solid surface can stimulate and activate T-cells in an antigen-specific manner, despite the absence of co-stimulatory molecules. This is likely attributable to sufficient numbers of TCRs on a T-cell binding to the MHC/peptide complexes that co-stimulation is unnecessary for activation.

In vivo applications of the disclosed polypeptides include the amelioration of conditions mediated by antigen-specific T-cells. Such conditions include allergies, transplant rejection and autoimmune diseases including multiple sclerosis, rheumatoid arthritis, systemic lupus erythematosus, and insulin-dependent diabetes mellitus. Other researchers have described various forms of MHC polypeptides that may be used to treat these conditions and the methods used in those systems are equally useful with the MHC polypeptides of the present invention. Exemplary methodologies are described in U.S. Pat. Nos. 5,130,297, 5,284,935, 5,468,481, 5,734,023 and 5,194,425. By way of example, the MHC/peptide complexes may be administered to patients in order to induce anergy in self-reactive T-cell populations, or these T-cell populations may be treated by administration of MHC/peptide complexes conjugated with a toxic moiety. The disclosed molecules may also be used to boost immune response in certain conditions such as cancer and infectious diseases.

EXAMPLES

The following Examples illustrate certain aspects of the invention.

Example 1
Cloning, Expression and In Vitro Folding of β1α1 Molecules

A prototypical nucleic acid construct was produced that encoded a single polypeptide chain with the amino terminus of the MHC class II α1 domain genetically linked to the carboxyl terminus of the MHC class II β1 domain. The sequence of this prototypical construct, made from the rat RT1B α- and β-chain cDNAs is shown in FIG. 1A (Seq I.D. No. 1).

RT1.B α1- and β1-domain encoding cDNAs were prepared by PCR amplification of cloned RT1.B α- and β-chain cDNA coding sequences (α6, β118, respectively) obtained from Dr. Konrad Reske, Mainz, FRG (Syha et al., 1989; Syha-Jedelhauser et al., 1991). The primers used to generate β1 were 5'-AATTCCTCGAGATGGCTCTGCAGACCCC-3' (XhoI 5' primer) (Seq. I.D. No. 9); 5'-TCTTGACCTC CAAGCCGCCGCAGGGAGGTG-3' (3' ligation primer) (Seq. I.D. No. 10) The primers used to generate α1 were 5'-CGGCGGCTTGGAGGTCAAGACGACATTGAGG-3' (5' ligation primer) (Seq. I.D. No. 11); 5'-GCCTCGGTACC TTAGTTGACAGCTTGGGTTGAATTTG-3' (KpnI 3' primer) (Seq. I.D. No. 12). Additional primers used were

```
5'-CAGGGACCATGGGCAGAGACTCCCCA-3'    (NcoI 5' primer) (Seq. I.D. No. 13); and 5'-GCCTCCTCGAGTTAGTTGACAGCTTGGGTT-3' (XhoI 3' primer) (Seq. I.D. No. 14).
```

Step one involved production of cDNAs encoding the β1 and α1 domains. PCR was conducted with Taq polymerase (Promega, Madison, Wis.) through 28 cycles of denaturation at 94.5° C. for 20 seconds, annealing at 55° C. for 1.5 minutes and extension at 72° C. for 1.5 minutes, using β118 as template and the XhoI 5' primer and 3' ligation primer as primers and α6 cDNA as template and the 5' ligation primer and KpnI 3' primer. PCR products were isolated by agarose gel electrophoresis and purified using Gene-Clean (Bio 101, Inc., La Jolla, Calif.).

In step two, these products were mixed together without additional primers and heat denaturated at 94.5° C. for 5 minutes followed by 2 cycles of denaturation at 94.5° C. for 1 minute, annealing at 60° C. for 2 minutes and extension at 72° C. for 5 minutes. In step three, the annealed, extended product was heat denaturated at 94.5° C. for 5 minutes and subjected to 26 cycles of denaturation at 94.5° C. for 20 seconds, annealing at 60° C. for 1 minute and extension at 72° C. for 1 minute, in the presence of the XhoI 5' primer and KpnI 3' primer. The final PCR product was isolated by agarose gel electrophoresis and Gene-Cleaned. This produced a 656 base pair cDNA encoding the β1α1 molecule. The cDNA encoding the β1α1 molecule was moved into cloning vector pCR2.1 (Invitrogen, Carlsbad, Calif.) using Invitrogen's TA Cloning® kit. The cDNA in pCR2.1 was used as template and PCR was conducted through 28 cycles of denaturation at 94.5° C. for 20 seconds, annealing at 55° C. for 1.5 minutes and extension at 72° C. for 1.5 minutes, using the NcoI 5' primer and XhoI 3' primer. The PCR products were cleaved with the relevant restriction enzymes and directionally cloned into pET21d+ (Novagen, Madison, Wis.; Studier et al., 1990). The constructs were confirmed by DNA sequencing. The β1α1 molecule used in these studies differs from wild-type in that it contains a beta-1 domain Q12R amino acid substitution.

For insertion of the peptide/linker cartridge (shown in FIG. 1A), the following approach was used. The 210 bp peptide/linker cartridge was amplified using the XhoI 5' primer and a primer of sequence:

```
5'-GAAATCCCGCGGGGAGCCTCCACCTCCA- (Seq. I.D. No. 15)

GAGCCTCGGGGCACTAGTGAGCCTCCACCTCCGAAGTGCACCACTGGGTTCTCA

TCCTGAGTCCTCTGGCTCTTCTGTGGGGAGTCTCTGCCCTCAGTCC-3'

(3'-MBP-72-89/linker ligation primer)
``` and the original full-length β118 cDNA as a template. A 559 bp cDNA with a 5' overhang for annealing to the peptide/linker cartridge cDNA was generated using a primer:ps 5'-GCTCCCCGCGGGATTTCGTGTACCAGTTCAA-3' (5' peptide/linker ligation primer) (Seq. I.D. No. 16); and the Kpn I 3' primer and the The 656 bp β1A1 cDNA as the amplification template. Annealing and extension of the two cDNAs resulted in the 750 bp full-length β1a1/MBP-72–89 construct. Modifications at the 5' and 3' ends of the β1α1 and β1a1/MBP-72–89 cDNAs were made for subcloning into pET21d+ (Novagen, Madison, Wis.; Studier et al., 1990) using the NcoI 5' primer and the XhoI 3' primer. The primers used to generate the MBP-55–69/linker cartridge were 5'-TATTACCATGGGCAGAGACTCCTCCGGCAAGGATTCGCATCATGCGGCGCGGAC
GACCCACTACGGTGGAGGTGGAGGCTCACTAGTGCCCC-3' (5' MBP-55-69 primer)

(Seq. I.D. No. 17) and

5'-GGGGCACTAGTGAGCCTCCACCTCCACCGTAGTGGGTCGTCCGCGCCGCATGAT
GCGAATCCTTGCCGGAGGAGTCTCTGCCCATGGTAATA-3' (3' MBP-55-69 primer)

(Seq. I.D. No. 18).

These were gel purified, annealed and then cut with NcoI and XhoI for ligation into β1a1/MBP-72–89 digested with NcoI and XhoI to produce a plasmid encoding the β1a1/MBP-55–69 covalent construct. The primers used to generate the Guinea pig MBP-72–89/linker cartridge were 5'-TATTACCATGGGCAGAGACTCCCCACAGAAGAGCCAGAGGTCTCAGGATGAGA
ACCCAGTGGTGCACTTCGGAGGTGGAGGCTCACTAGTGCCCC-3' (5' Gp-MBP-72-89 primer)

(Seq. I.D. No. 28) and

5'-GGGGCACTAGTGAGCCTCCACCTCCGAAGTGCACCACTGGGTTCTCATCCTGA
GACCTCTGGCTCTTCTGTGGGGAGTCTCTGCCCATGGTAAT-3' (3'Gp-MBP-72-89 primer)

(Seq. I.D. No. 29).

These were gel purified, annealed and then cut with NcoI and XhoI for ligation into β1a1/MBP-72–89 digested with NcoI and XhoI, to produce a plasmid encoding the β1a1/Gp-MBP-72–89 covalent construct. The primers used to generate the CM-2/linker cartridge were 5'-TATTACCATGGGCAGAGACTCCAAACTGGAACTGCAGTCCGCTCTGGAAGAAGC
TGAAGCTTCCCTGGAACACGGAGGTGGAGGCTCACTAGTGCCCC-3' (5' CM-2 primer)

(Seq. I.D. No. 19) and

5'-GGGGCACTAGTGAGCCTCCACCTCCGTGTTCCAGGGAAGCTTCAGCTTCTTCCA
GAGCGGACTGCAGTTCCAGTTTGGAGTCTCTGCCCATGGTAATA-3' (3' CM-2 primer)

(Seq. I.D. No. 20).

These were gel purified, annealed and then cut with NcoI and XhoI for ligation into β1a1/MBP-72–89 digested with NcoI and XhoI, to produce a plasmid encoding the β1a1/CM-2 covalent construct.

Protein expression was tested in a number of different *E. coli* strains, including a thioredoxin reductase mutant which allows disulfide bond formation in the cytoplasm (Derman et al., 1993). With such a small molecule, it became apparent that the greatest yield of material could be readily obtained from inclusion bodies, refolding the protein after solubilization and purification in buffers containing 6M urea. Accordingly, *E. coli* strain BL21(DE3) cells were transformed with the pET21d+ construct containing the β1α1-encoding sequence. Bacteria were grown in one liter cultures to mid-logarithmic phase ($OD_{600}$=0.6–0.8) in Luria-Bertani (LB) broth containing carbenicillin (50 μg/ml) at 37° C. Recombinant protein production was induced by addition of 0.5 MM isopropyl β-D-thiogalactoside (IPTG). After incubation for 3 hours, the cells were centrifuged and stored at −80° C. before processing. All subsequent manipulations of the cells were at 4° C. The cell pellets were resuspended in ice-cold PBS, pH 7.4, and sonicated for 4×20 seconds with the cell suspension cooled in a salt/ice/water bath. the cell suspension was then centrifuged, the supernatant fraction was poured off, the cell pellet resuspended and washed three times in PBS and then resuspended in 20 mM ethanolamine/6 M urea, pH 10, for four hours. After centrifugation, the supernatant containing the solubilized recombinant protein of interest was collected and stored at 4° C. until purification. Recombinant β1α1 construct was purified and concentrated by FPLC ion-exchange chromatography using Source 30Q anion-exchange media (Pharmacia Biotech, Piscataway, N.J.) in an XK26/20 column (Pharmacia Biotech), using a step gradient with 20 mM ethanolamine/6M urea/1M NaCl, pH 10. The homogeneous peak of the appropriate size was collected, dialyzed extensively against PBS at 4° C., pH 7.4, and concentrated by centrifugal ultrafiltration with Centricon-10 membranes (Amicon, Beverly, Mass.). The dialysis step, which removed the urea from the protein preparation and reduced the final pH, resulted in spontaneous re-folding of the expressed protein. For purification to homogeneity, a finish step used size exclusion chromatography on Superdex 75 media (Pharmacia Biotech) in an HR16/50 column (Pharmacia Biotech). The final yield of purified protein varied between 15 and 30 mg/L of bacterial culture.

Conformational integrity of the molecules was demonstrated by the presence of a disulfide bond between cysteines β15 and β79 as detected on gel shift assay, and the authenticity of the purified protein was verified using the OX-6 monoclonal antibody specific for RT1B by Western Blotting (data not shown). Circular dichroism (CD) reveals that the β1α1 molecules have highly ordered secondary structures. The empty β1α1 molecule contains approximately 30% alpha-helix, 15% beta-strand, 26% beta-turn, and 29% random coil structures. Comparison with the secondary structures of class II molecules determined by x-ray crystallography provides strong evidence that the β1α1 molecules share the beta-sheet platform/anti-parallel alpha-helix secondary structure common to all class II antigen binding domains. Furthermore, thermal denaturation revealed a high degree of cooperativity and stability of the molecules (data not shown).

Example 2
β1α1 Molecules Bind T Lymphocytes in an Epitope-Specific Manner

The β1α1 molecule produced as described above was tested for efficacy (T-cell binding specificity) using the Experimental Autoimmune Encephalomyelitis (EAE) system. EAE is a paralytic, inflammatory, and sometimes demyelinating disease mediated by CD4+ T cells specific for central nervous system myelin components including myelin basic protein (MBP). EAE shares similar immunological abnormalities with the human demyelinating disease MS (Paterson, 1981) and has been a useful model for testing preclinical therapies for the human illness (Weiner et al, 1993; Vandenbark et al., 1989; Howell et al., 1989; Oksenberg et al., 1993; Yednock et al, 1992; Jameson et al., 1994; Vandenbark et al., 1994). In Lewis rats, the dominant encephalitogenic MBP epitope resides in the 72–89 peptide (Bourdette et al., 1991). Onset of clinical signs of EAE occurs on day 10–11, and the disease lasts four to eight days. The majority of invading T lymphocytes are localized in the CNS during this period.

Materials and Methods

Test and control peptides for loading into the purified β1α1 molecule were synthesized as follows: Gp-MBP-69–89 peptide (GSLPQKSQRSQDENPVVHF) (Seq. I.D. No.25), rat-MBP-69–89 peptide (GSLPQKSQRT QDENPVVHF) (Seq. I.D. No. 30), Gp-MBP-55–69 peptide (SGKDSHHAARTTHYG) (Seq. I.D. No. 26), and cardiac myosin peptide CM-2 (KLELQSALEEA3EASLEH) (Seq. I.D. No. 27) (Wegmann et al., 1994) were prepared by solid-phase techniques (Hashim et al., 1986). The Gp-MBP peptides are numbered according to the bovine MBP sequence (Vandenbark et al., 1994; Martenson, 1984). Peptides were loaded onto β1α1 at a 1:10 protein:peptide molar ratio, by mixing at room temperature for 24 hours, after which all subsequent manipulations were performed at 4° C. Free peptide was then removed by dialysis or centrifugal ultrafiltration with Centricon-10 membranes, serially diluting and concentrating the solution until free peptide concentration was less than 2 μM.

T-cell lines and the A1 hybridoma were prepared as follows: Short-term T-lymphocyte lines were selected with MBP-69–89 peptide from lymph node cells of naive rats or from rats immunized 12 days earlier with Gp-MBP/CFA as described by Vandenbark et al., 1985) The rat Vβ8.2+ T cell hybridoma C14/BW12-12A1 (A1) used in this study has been described previously by Burrows et al., 1996). Briefly, the A1 hybridoma was created by fusing an encephalitogenic LEW(RT1$^{1'}$) T cell clone specific for Gp-BP-72–89 (White et al., 1989; Gold et al, 1991) with a TCR (α/β) negative thymoma, BW5147 (Golding et al., 1985). Wells positive for cell growth were tested for IL-2 production after stimulation with antigen in the presence of APCs (irradiated Lewis rat thymocytes) and then subcloned at limiting dilution. The A1 hybridoma secretes IL-2 when stimulated in the presence of APCs with whole Gp-BP or Gp-BP-69–89 peptide, which contains the minimum epitope, MBP-72–89.

Two color immunofluorescent analysis was performed on a FACScan instrument (Becton Dickinson, Mountain View, Calif.) using CellQues™ software. Quadrants were defined using non-relevant isotype matched control antibodies. β1α1 molecules with and without loaded peptide were incubated with the A1 hybridoma (10 μM β1α1/peptide) for 17 hours, 4° C., washed three times, stained with fluorochrome (FITC or PE) conjugated antibodies specific for rat class II (OX6-PE), and TCR Vβ8.2 (PharMingen, San Diego, Calif.) for 15 minutes at room temperature, and analyzed by flow cytometry. The CM-2 cell line was blocked for one hour with unconjugated OX6, washed and then treated as the A1 hybridoma. Staining media was PBS, 2% fetal bovine serum, 0.01% azide.

Results

Epitope-specific binding was evaluated by loading the β1α1 molecule with various peptides and incubating β1α1/peptide complexes with the A1 hybridoma that recognizes the MBP-72–89 peptide (Burrows et al., 1997), or with a cardiac myosin CM-2-specific cell line. As is shown in FIG. 3A, the β1α1 construct loaded with MBP-69–89 peptide (β1α1/MBP-69–89) specifically bound to the A1 hybridoma, with a mean fluorescence intensity (MFI) of 0.8×10³ Units, whereas the β1α1 construct loaded with CM-2 peptide (β1α1/CM-2) did not stain the hybridoma. Conversely, β1α1/CM-2 specifically bound to the CM-2 line, with a MFI of 1.8×10³ Units, whereas the β1α1/MBP-69–89 complex did not stain the CM-2 line (FIG. 3B). The β1α1 construct without exogenously loaded peptide does not bind to either the A1 hybridoma (FIG. 3A) nor the CM-2 line (data not shown). Thus, bound epitope directed the specific binding of the β1α1/peptide complex.

Example 3
β1α1 Molecules Conjugated with A Fluorescent Label

Figure 4:
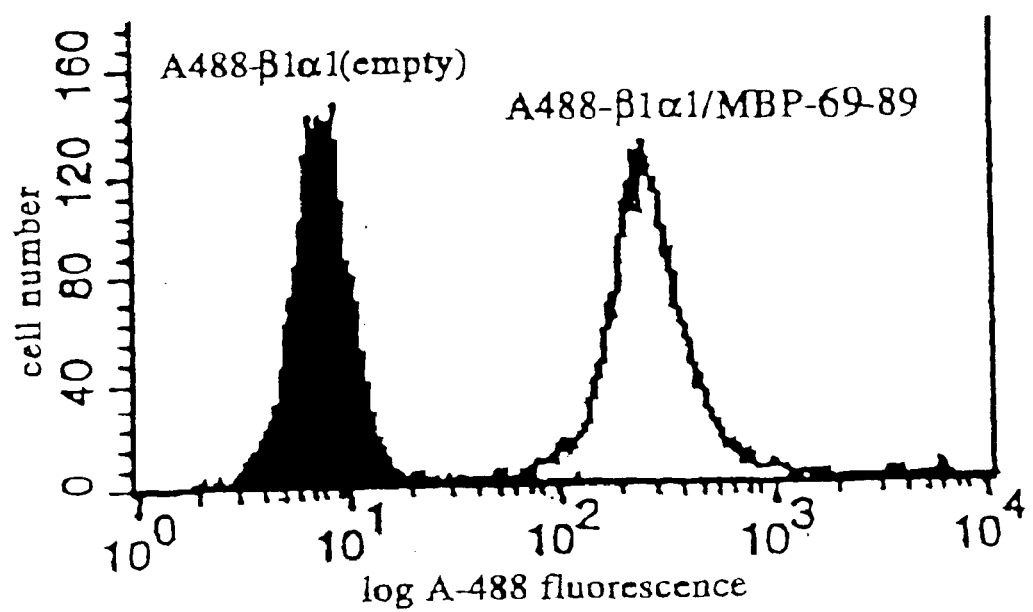

To avoid using a secondary antibody for visualizing the interaction of β1α1/peptide molecules with TCR (such as OX-6, used above), a β1α1 molecules directly conjugated with a chromophore was produced. The Alexa-488™ dye (A488; Molecular Probes, Eugene, Oreg.) has a spectra similar to fluorescein, but produces protein conjugates that are brighter and more photo-stable than fluorescein conjugates. As is shown in FIG. 4, A488-conjugated β1α1 (molar ratio dye/protein=1), when loaded with MBP-69–89, bound to the A1 hybridomas (MCI=300 Units), whereas empty β1α1 did not.

Example 4
β1α1 Molecules Inhibit Epitope-Specific T-cell Proliferation In Vitro

T-cell proliferation assays were performed to evaluate the effect of the constructs on T cell activation.

Materials and Methods

Proliferation assays were performed in 96-well plates as described previously (Vandenbark et al., 1985). Briefly, 4×10⁵ cells in 200 μl/well (for organ stimulation assays) or 2×10⁴ T cells and 1×10⁶ irradiated APCs (for short-term T cell lines) were incubated in RPMI and 1% rat serum in triplicate wells with stimulation medium only, Con A, or antigen with or without supplemental IL-2 (20 Units/ml) at 37° C. in 7% CO₂. The cultures were incubated for three (lays, the last 18 hr in the presence of [³H]thymidine (0.5

µCi/10 µl/well). The cells were harvested onto glass fiber filters and [$^3$H]thymidine uptake assessed by liquid scintillation. In some experiments, the T cells were pretreated 24 hours with β1α1 constructs (with and without loaded peptides), washed, and then used in proliferation assays with and without IL-2, as above. Mean counts per minute ±SD were calculated from triplicate wells and differences between groups determined by Student's t-test.

Results

Figure 5:
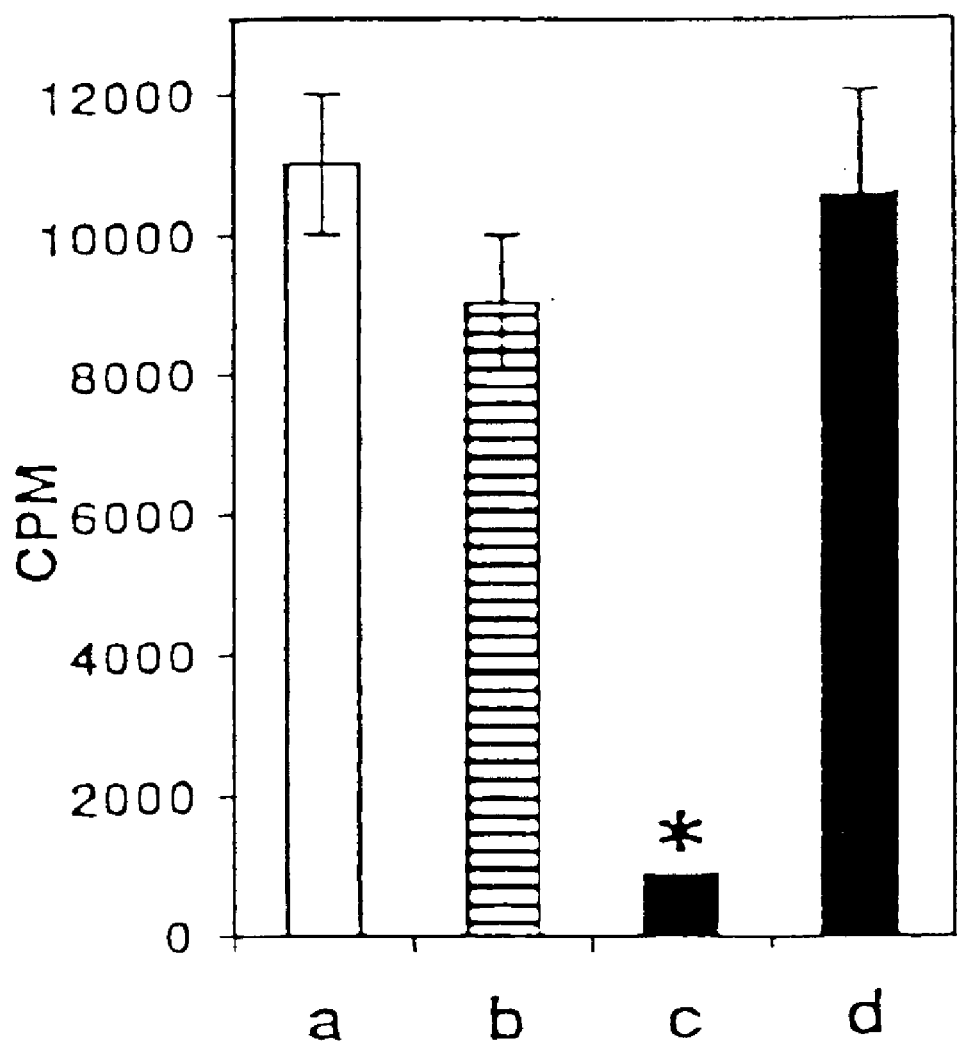

A range of concentrations (10 nM to 20 µM) of peptide-loaded β1α1 complexes were pre-incubated with an MBP-69–89 specific T cell line prior to stimulation with the MBP-69–89 peptide+APC (antigen-presenting cell). As is shown in FIG. 5, pre-treatment of MBP-69–89 specific T cells with 10 nM β1α1/MBP-69–89 complex significantly inhibited proliferation (>90%), whereas pre-incubation with 20 µM β1α1/MBP-55–69 complex produced a nominal (27%) but insignificant inhibition. Of mechanistic importance, the response inhibited by the β1α1/MBP-69–89 complex could be fully restored by including 20 Units/ml of IL-2 during stimulation of the T cell line (FIG. 5) suggesting that the T-cells had been rendered anergic by exposure to the β1α1/MBP-69–89 complex.

Example 5
Antigen-Loaded β1α1 Molecules Suppress and Treat EAE

The β1α1/MBP-69–89 complex was evaluated for its ability to suppress the induction, as well as to treat existing signs of EAE in Lewis rats.

Materials and Methods

Female Lewis rats (Harlan Sprague-Dawley, Inc., Indianapolis, Ind.), 8–12 weeks of age, were used for clinical experiments in this study. The rats were housed under germ-free conditions at the Veterans Affairs Medical Center Animal Care Facility, Portland, Oreg., according to institutional guidelines. Active EAE was induced in the rats by subcutaneous injection of 25 µg guinea pig myelin basic protein (GP-MBP) or 200 µg GP-MBP-69–89 peptide in Freund's complete adjuvant supplemented with 100 or 400 µg Mycobacterium tuberculosis strain H37Ra (Difco, Detroit, Mich.), respectively. The clinical disease course induced by the two emulsions was essentially identical, with the same day of onset, duration, maximum severity, and cumulative disease index. The rats were assessed daily for changes in clinical signs according to the following clinical rating scale: 0, no signs; 1, limp tail; 2, hind leg weakness, ataxia; 3, paraplegia; and 4, paraplegia with forelimb weakness, moribund condition. A cumulative disease score was obtained by summing the daily disability scores over the course of EAE for each affected rat, and a mean cumulative disease index (CDI) was calculated for each experimental group.

Spinal cord mononuclear cells were isolated by a discontinuous percol gradient technique and counted as previously described (Bourdette et al., 1991). The cells were stained with fluorochrome (FITC or PE) conjugated antibodies specific for rat CD4, CD8, CD11b, CD45ra, TCR Vβ8.2 and CD134 (PharMingen, San Diego, Calif.) for 15 min at room temperature and analyzed by flow cytometry. The number of positive staining cells per spinal cord was calculated by multiplying the percent staining by the total number of cells per spinal cord. Control and β1α1/MBP-69–89 protected rats were sacrificed at peak and recovery of clinical disease, spinal cords were dissected and fixed in 10% buffered formalin. The spinal cords were paraffin-embedded and sections were stained with luxol fast blue-periodic acid schiff-hematoxylin for light microscopy.

Results

Figure 6C:
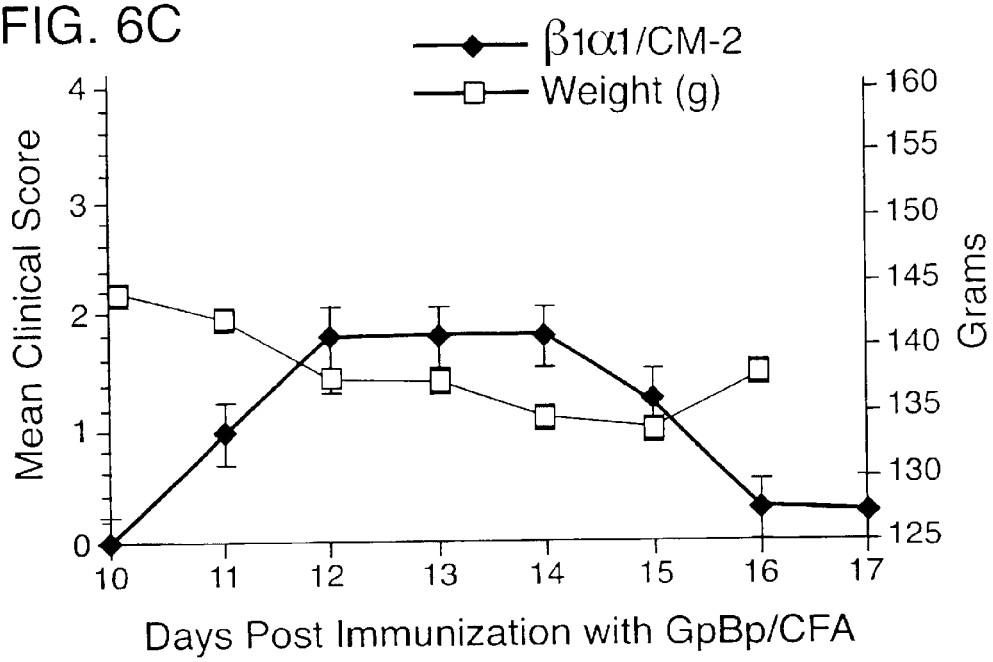
Figure 6D:
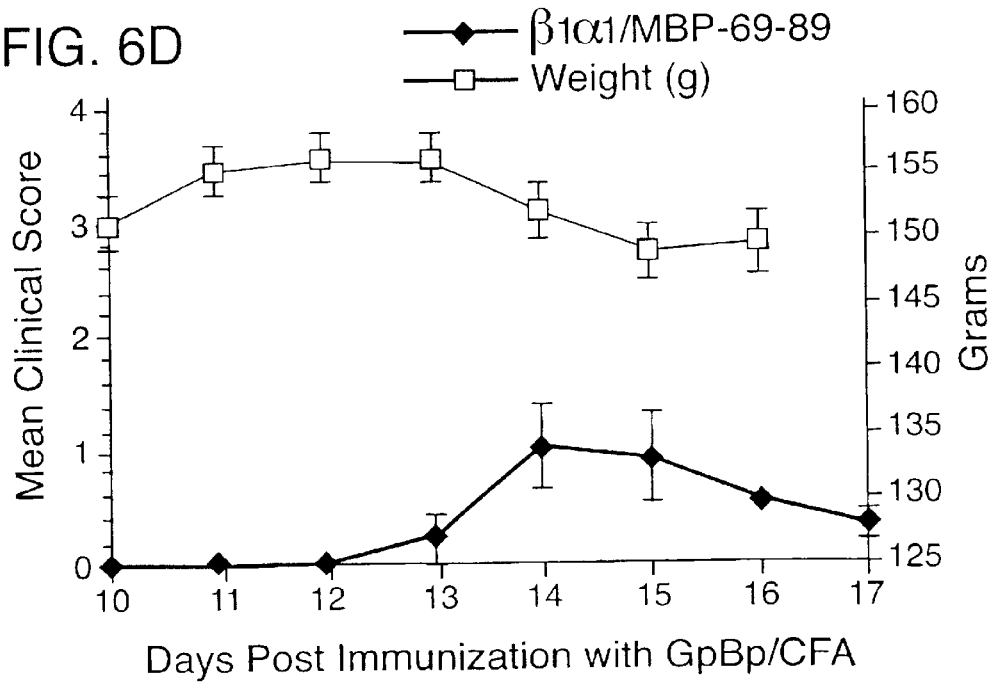

Intravenous injection (i.v.) of 300 µg of the β1α1/MBP-69–89 complex in saline on days 3, 7, 9, 11, and 14 after injection of MBP or MBP-69–89 peptide in CFA suppressed the induction of clinical (FIG. 6 and Table 3) and histological (not shown) signs of EAE. Injection of as little as 30 µg of the β1α1/MBP-69–89 complex following the same time course was also effective, completely suppressing EAE in 4 of 6 rats, with only mild signs in the other 2 animals. All of the control animals that were untreated, that received 2 µg MBP-69–89 peptide alone (the dose of free peptide contained in 30 µg of the complex), or that received 300 µg of the empty β1α1 construct developed a comparable degree of paralytic EAE (Table 2). Interestingly, injection of 300 µg of a control β1α1/CM-2 peptide complex produce a mild (about 30%) suppression of EAE (FIG. 6 and Table 2). In parallel with the course of disease, animals showed a dramatic loss in body weight (FIG. 6), whereas animals treated with the β1α1/MBP-69–89 complex showed no significant loss of body weight throughout the course of the experiment.

TABLE 2

Effect of β1α1/peptide complexes on EAE in Lewis rats.

| Treatment of EAE[a] | Incidence | Day of Onset | Duration (days) | Maximum Disease Score | Cumulative Disease Index |
|---|---|---|---|---|---|
| Untreated[b] | 11/11 | 12 ± 1[c] | 5 ± 1 | 2.9 ± 0.3 | 10.0 ± 2.2 |
| 2 µg MBP-69-89 | 6/6 | 12 ± 1 | 6 ± 1 | 3.3 ± 0.3 | 11.2 ± 1.9 |
| β1α1/(empty) 300 µg | 5/5 | 12 ± 1 | 6 ± 1 | 2.9 ± 0.6 | 9.7 ± 2.1 |
| β1α1/CM-2 300 µg | 5/5 | 12 ± 1 | 6 ± 2 | 1.9 ± 0.8 | 7.2 ± 2.6* |
| β1α1/MBP-69-89 300 µg | 0/6* | — | — | 0 ± 0** | 0 ± 0** |
| β1α1/MBP-69-89 30 µg | 2/6 | 14 ± 0 | 4 ± 0 | 0.2 ± 0.1** | 0.7 ± 0.3** |

[a]EAE was induced with either Gp-BP/CFA or MBP-69-89/CFA.
[b]Combined controls from two experiments.
[c]Values represent the mean ± S.D.
*P ≤ 0.05
**P ≤ 0.01

TABLE 3

Characterization of infiltrating spinal cord cells at the peak of
EAE in control and β1α1/MBP-69–89 protected rats.

| Spinal cord | Total* | OX40+ | Vβ8.2+ | Vβ8.2+/OX40+ |
|---|---|---|---|---|
| Protected | 200 | 38 | 10 | 5 |
| Control | 7500 | 1750 | 980 | 667 |

*Number of cells/spinal cord × $10^{-3}$

To evaluate the effect of the construct on established disease, Lewis rats were treated with 300 μg of the β1α1/MBP-69–89 complex on the first day of disease onset, with follow-up injections 48 and 96 hours later. EAE in the control rats progressed to complete hind limb paralysis, whereas no progression of the disease occurred in any of the treated animals (FIG. 7). The mild course of EAE (mean cumulative index, MCI=3±0.13) in the treated group was significantly less than the severe course of EAE in the control group (MCI=11.2±2.7, p=0.013), although the duration of disease (6 days) was the same in both groups.

Consistent with the complete lack of inflammatory lesions in spinal cord histological sections (not shown), suppression of EAE with the β1α1/MBP-69–89 complex essentially eliminated the infiltration of activated inflammatory cells into the CNS. Mononuclear cells were isolated from the spinal cords of control and protected animals at peak and recovery of clinical disease and examined by FACS analysis. The total number of mononuclear cells isolated from spinal cords of control animals at peak of clinical disease (day 14) was 40-fold higher than from protected animals evaluated at the same time point (Table 3). Moreover, protected animals had 72% fewer activated (OX40+), Vβ8.2+ T cells in the spinal cord when compared to control animals (Table 3). CD4+ and CD8+ T cells, macrophages and B cell numbers were also significantly reduced in protected animals (not shown). The number of mononuclear cells isolated after recovery from EAE was reduced 4.5-fold in protected animals ($0.64×10^5$ cells/spinal cord) compared to control animals ($2.9×10^5$ cells/spinal cord). Protected animals also had 10-fold fewer activated (OX40+), Vβ8.2+ T cells in the spinal cord than control animals after recovery from disease.

Figure 8A:
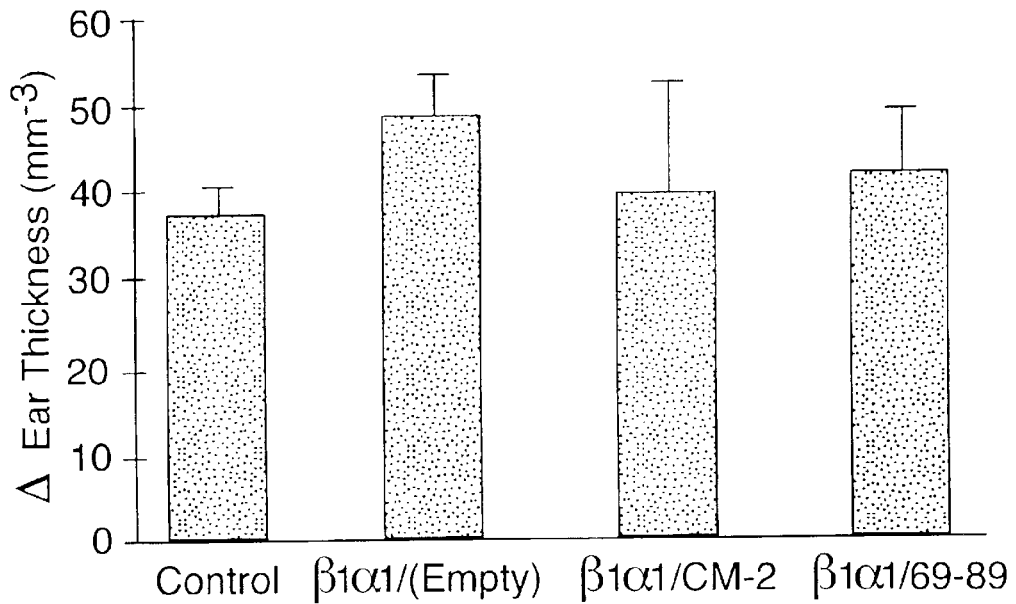
Figure 8B:
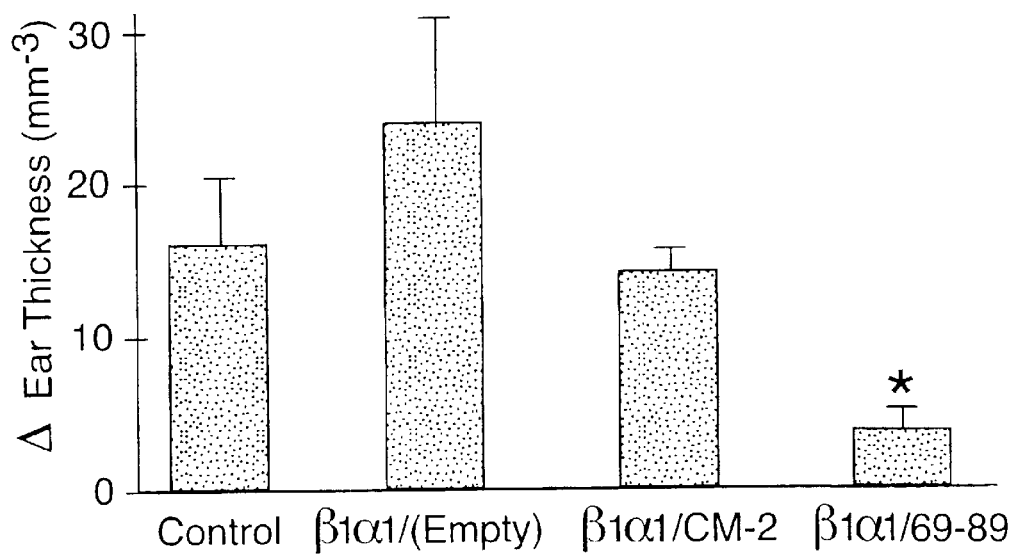

Treatment with β1α1/MBP-69–89 complex specifically inhibited the delayed-type hypersensitivity (DTH) response to MBP-69–89. As shown in FIG. 8A, changes in ear thickness 24 hours after challenge with PPD were uneffected by in animals treated with β1α1 or β1α1 loaded with peptides. However, as is shown in FIG. 8B, while animals treated with β1α1 alone or complexed with CM-2 had no effect on the DTH response, animals treated with the β1α1/MBP-69–89 complex showed a dramatic inhibition of the DTH response to MBP-69–89.

Treatment of EAE with the β1α1/MBP-69–89 complex also produced an inhibition of lymph node (LN) T cell responses. As is shown in FIG. 9, LN cells from rats treated with the suppression protocol (FIG. 6) were inhibited 2–4 fold in response to MBP or the MIP-69–89 peptide compared to control rats. This inhibition was antigen specific, since LN T cell responses to PPD (stimulated by the CFA injection) were the same in treated and control groups. T cell responses tested in rats treated after disease onset (FIG. 7) were also inhibited, in an IL-2 reversible manner. LN cell responses to MBP and MBP-69–89 peptide were optimal (S.I=4–5×) at low antigen (Ag) concentrations (4 μg/ml), and could be enhanced 2-fold with additional IL-2. In contrast, responses were inhibited in treated rats, with optimal LN cell responses (±3×) requiring higher Ag concentrations (20–50 μg/ml). However, in the presence of IL-2, responses could be restored to a level comparable to control rats (S.I.=6–11×) without boosting Ag concentrations.

Discussion

The following Examples illustrate the efficacy of the two-domain MHC molecules.

While the experimental details concern the MHC class II β1α1 polypeptides, it will be appreciated that these data fully support application of MHC class I α1α2 polypeptides.

In the presented Examples, polypeptides comprising the MHC class II β1 and α1 domains are described. These molecules lack the α2 domain, the β2 domain known to bind to CD4, and transmembrane and intra-cytoplasmic sequences. The reduced size and complexity of the β1α1 construct permits expression and purification of the molecules from bacterial inclusion bodies in high yield. The β1α1 molecules are shown to refold in a manner that allows binding of allele-specific peptide epitopes and to have excellent solubility in aqueous buffers. When complexed with peptide antigen, direct detection of the β1α1/peptide complexes to T cells can be visualized by FACS, with the specificity of binding determined by the peptide antigen. The β1α1/69–89 complex exerted powerful and selective inhibitory effects on T cell activation in vitro and in vivo. Because of its simplicity, biochemical stability, biological properties, and structural similarity with human class II homologs, the β1α1 construct represents a template for producing a novel class of TCR ligands.

Direct binding studies using the A1 hybridoma specific for MBP-72–89 showed distinct staining with β1α1/MBP-69–89, with a 10-fold increase in MFI over background, and was not stained with β1α1/CM-2 nor "empty" β1α1. In a reciprocal manner, binding studies using a CM-2 specific cell line showed strong staining with β1α1/CM-2 and no staining with β1α1/MBP-69–89. Thus, bound epitope directed specific interaction of the β1α1/peptide complexes. Identification of antigen-specific T cells has been possible in a few systems (McHeyzer et al., 1995; MacDonald et al., 1993; Walker et al., 1995; Reiner et al., 1993), using labeled anti-idiotypic T cell receptor antibodies as specific markers, but the general approach of staining specific T cells with their ligand has failed because soluble peptide-MHC complexes have an inherently fast dissociation rate from the T cell antigen receptor (Corr et al., 1995; Matsui et al., 1994; Syulkev et al., 1994). Multimeric peptide-MHC complexes containing four-domain soluble MHC molecules have been used to stain antigen-specific T lymphocytes (Altman et al., 1996), with the ability to bind more than one T cell receptor (TCR) on a single T cell presumably giving the multimeric molecules a correspondingly slower dissociation rate. Staining with β1α1/peptide complexes, while specific, did take an incubation period of approximately 10 hours to saturate (data not shown). The extraordinarily bright staining pattern of the A1 hybridoma with the β1α1/MBP-69–89 complex, and the CM-2 line with β1α1/CM-2, coupled with the length of time it takes to achieve binding saturation, suggests that this molecule might have a very slow off-rate once bound to the TCR. These complexes and modified versions of them would be unusually well suited to directly label antigen-specific T cells for purposes of quantification and recovery.

The β1α1/peptide complex was highly specific in its ability to bind to and inhibit the function of T cells. In vitro proliferation of MBP-specific T cells was inhibited >90% with the β1α1/MBP-69–89 complex, and in vivo there was a nearly complete inhibition of clinical and histological EAE.

The most profound biological activity demonstrated for β1α1/MBP-69–89 was its ability to almost totally ablate the encephalitogenic capacity of MBP-69–89 specific T cells in vivo. Injection of this complex after initiation of EAE nearly completely suppressed clinical and histological signs of EAE, apparently by directly inhibiting the systemic activation of MBP-69–89 specific T cells, and preventing recruitment of inflammatory cells into the CNS. Moreover, injection of β1α1/MBP-69–89 after onset of clinical signs arrested disease progression, demonstrating the therapeutic potential of this molecular construct. Interestingly, the effect of the complex on already activated T cells was not only to inhibit stimulation, but also to reduce sensitivity to antigen, with optimal activation after treatment requiring a 10-fold increase in antigen concentration.

From a drug engineering and design perspective this prototypic molecule represents a major breakthrough. The demonstrated biological efficacy of the β1α1/MBP-69–89 complex in EAE raises the possibility of using this construct as a template for engineering human homologs for treatment of autoimmune diseases such as multiple sclerosis, that likely involves inflammatory T cells directed at CNS proteins. One candidate molecule would be HLA-DR2/MBP-84–102, which includes both the disease-associated class II allele and a known immunodominant epitope that has been reported to be recognized more frequently in MS patients than controls. However, because of the complexity of T cell response to multiple CNS proteins and their component epitopes, it is likely that a more general therapy may require a mixture of several MHC/Ag complexes. The precision of inhibition induced by the novel β1α1/MBP-69–89 complex reported herein represents an important first step in the development of potent and selective human therapeutic reagents. With this new class of reagent, it may be possible to directly quantify the frequency and prevalence of T cells specific for suspected target autoantigens, and then to selectively eliminate them in affected patients. Through this process of detection and therapy, it may then be possible for the first time to firmly establish the pathogenic contribution of each suspected T cell specificity.

Having illustrated and described the principles of synthesizing two domain class II β1α1 and class I α1α2 molecules and the methods of using such molecules, it will be apparent to one skilled in the art that the invention can be modified in arrangement and detail without departing from such principles. We claim all modifications coming within the spirit and scope of the claims presented herein.

References

Altman, J. D. et al. Phenotypic analysis of antigen-specific T lymphocytes. *Science* 274, 94–96 (1996).

Arimilli, S., Cardoso, C., Mukku, P., Baichwal, V. & Nag, B. Refolding and reconstitution of functionally active complexes of human leukocyte antigen DR2 and myelin basic protein peptide from recombinant alpha and beta polypeptide chains. Journal of Biological Chemistry 270(2), 971–977 (1995 ).

Auffray et al. (1984). Isotypic and allotypic variation of human class II histocompatibility antigen alpha-chain genes. Nature 308 (5957), 327–333.

Ausubel et al. (198,7). In *Current Protocols in Molecular Biology*, Greene Publishing Associates and Wiley-Intersciences.

Benoist et al. (1983). The murine Ia alpha chains, E alpha and A alpha, show a surprising degree of sequence homology. Proc. Natl. Acad. Sci. U.S.A. 80 (2), 534–538.

Boniface, J. J. & Davis, M. M. T-cell recognition of antigen. A process controlled by transient intermolecular interactions. *Annals New York Acad. Sciences*. 766, 62–69 (1995).

Bourdette, D. N. et al. Myelin basic protein specific T cells in the CNS and lymph nodes of rats with EAE are different. *J. Neurosci. Res.* 30, 308–315 (1991).

Brown, J. H., Jardetzky, T. S., Gorga, J. C., Stern, L. J., Urban, R. G. & Strominger, J. L Three dimensional structure of the human class II histocompatibility antigen HLA-DR1. *Nature* 364, 33–39 (1993).

Browning et al., (1995). The HLA-A, B,C genotype of the class I negative cell line Daudi reveals novel HLA-A and -B alleles. Tissue Antigens 45 (3), 177–187.

Burrows, G. G. et al. Variation in H-2K$^k$ peptide motif revealed by sequencing naturally processed peptides prom T cell hybridoma class I molecules. *J. Neurosci. Res.* 45, 803–811 (1996).

Burrows, G. G. et al. Multiple Class I Motifs Revealed by Sequencing Naturally Processed Peptides Eluted from Rat T Cell MHC Molecules. *Rapid Communication. J. Neurosci. Res.* 49, 107–116 (1997).

Cammarota, G. et al. Identification of a CD4 binding site on the $b_2$ domain of HLA-DR molecules. Nature 356, 799–801 (1992).

Caspi, R. R. et al. A new model of autoimmune disease: Experimental autoimmune uveorentinitis induced in mice with two different retinal antigens. *J. Immunol.* 140, 1490–1495 (1988).

Chaurhary et al. (1989). Nature 339: 394–397.

Cobbold, S. P., Nash, J. A., Prospero, T. D. & Waldham, H. Therapy with monoclonal antibodies by elimination of T-cell subsets in vivo. *Nature* 312, 548–551 (1988).

Cobbold, S. P., Nash, J. A., Prospero, T. D. & Waldham, H. Therapy with monoclonal antibodies by elimination of T-cell subsets in vivo. *Nature* 312, 548–551 (1988).

Collins et al. Nature 371 (6498): 626–629 (1994).

Corr, M. et al. T cell receptor-MHC class I peptide interactions: affinity, kinetics, and specificity. *Science* 265, 946–949 (1995).

Cush, J. J. & Lipsky, P. E. Phenoytpic analysis of synovial tissue and peripheral blood lymphocytes isolated from patients with rheumatoid arthritis. *Arthritis Rheum.* 31, 1230–1238 (1988).

Das et al. (1983). Structure and nucleotide sequence of the heavy chain gene of HLA-DR. proc. Natl. Acad. Sci. U.S.A. 80 (12), 3543–3547.

Derman, A. I., Prinz, W. A., Belin, D. & Beckwith, J. Mutations that allow disulfide bond formation in the cytoplasm of *Escherichia coli. Science* 262, 1744–1747 (1993).

Desbarats, J., Freed, J. H., Campbell, P. A., & Newell, M. K. Fas (CD95) expression and death-mediating function are induced by CD4 cross-linking on CD4+ T cells. *PNAS* 93, 11014–11018 (1996).

Edwards et al. *Science* 276 (5320): 1868–1871 (1997).

Estess et al. (1986). Sequence analysis and structure-function correlations of murine q, k, u, s, and f haplotype I-A beta cDNA clones. Proc. Natl. Acad. Sci. U.S.A. 83 (11), 3594–3598.

Ferrin, T. E., Huang, C. C., Jarvis, L. E. & Langridge, R. The MIDAS display system. *J. Mol. Graphics* 6, 13–27 (1988).

Fleury et al., CELL 66, 1037–1049 1991

Fremont, et al. Structures of an MHC class II molecule with covalently bound single peptides. Science 2,72, 1001–1004 (1996).

Gold, D. P., H. Offner, D. Sun, S. Wiley, A. A. Vandenbark and D. B. Wilson. 1991. Analysis of T cell receptor βchains in Lewis rats with experimental autoimmune encephalomyelitis: Conserved complementarity determining region 3. *J. Exp. Med.* 174:1467.

Golding, H., J. McCluskey, T. I. Munitz, R. N. Germain, D. H. Margulies and A. Singer. 1985. T-cell recognition of a chimaeric class II/class I MHC molecule and the role of L3T4. *Nature*, 317:425.

Govaerts, A. et al. HLA and multiple sclerosis: population and family studies. *Tissue Antigens* 25, 187–199 (1985).

Harlow and Lane (1988). *Antibodies, A Laboratory Manual*, Cold Spring Harbor Laboratory, New York.

Hashim, G. A., Day, E. D., Fredane, L., Intintola, P., and Carvalho, E. Biological activity of region 65 to 102 of the myelin basic protein. *J. Neurosci. Res.* 16, 467–478 (1986).

Housset, D., Habersetzer Rochat, C., Astier, J. P. & Fontecilla-Camps, J. C. Crystal structure of toxin II from the scorpion *Androctonus Australis Hector* refined at 1.3 angstroms resolution. *J. Mol. Biol.* 238, 88 (1994).

Howell, M. D. et al. Vaccination against experimental allergic encephalomyelitis with T-cell receptor peptides. *Science* 246, 668–670 (1989).

Huang, B., Yachou, A., Fleury, S., Hendrickson, W. & Sekaly, R. Analysis of the contact sites on the CD4 molecule with class II MHC molecule. *J. Immunol.* 158, 216–225 (1997).

Innis et al. (1990). *PCR Protocols, A Guide to Methods and Applications*, Innis et al. (eds.), Academic Press, Inc., San Diego, Calif.

Jameson, B. A., McDonnel, J. M., Marini, J. C. & Korngold, R. A rationally designed CD4 analogue inhibits experimental allergic encephalomyelitis. *Nature* 368, 744–746 (1994).

Janeway & Travers (1997). *Immunobiology: the immune system in health and disease*, Current Biology Ltd./Garland Publishing, Inc. New York.

Kato et al., (1993). Molecular analysis of HLA-B39 subtypes. Immunogenetics 37 (3), 212–216.

Kelly & Trowsdale. (1985). Complete nucleotide sequence of a functional HLA-DP beta gene and the region between the DP beta 1 and DP alpha 1 genes: comparison of the 5' ends of HLA class II genes Nucleic Acids Res. 13 (5), 1607–1621.

King, J. and Leimmli, U. K. Bacteriophage T4 tail assembly: structural proteins and their genetic identification. *J. Mol. Biol.* 75, 315–337 (1973).

Konig, R., Shen, X. & Germain, R. N. Involvement of both major histocompatibility complex class II α and β chains in CD4 function indicates a role for ordered oligomerization in T cell activation. *J. Exp. Med.* 182, 779–787 (1995).

König, R., Huang, L. Y. & Germain, R. MHC class II interaction with CD4 mediated by a region analogous to the MHC class I binding site for CD8. *Nature* 356, 796–798 (1992).

Kozono, H., White, J., Clements, J., Marrack, P. & Kappler, J. Production of soluble MHC class II proteins with covalently bound single peptides. *Nature* 369, 151 –154 (1994).

Kress et al., (1983). Alternative RNA splicing in expression of the H-2K gene. Nature 306 (5943), 602–604.

Larhammar et al. (1983). Exon-intron organization and complete nucleotide sequence of a human major histocompatibility antigen DC beta gene. Proc. Natl. Acad. Sci. U.S.A. 80 (23), 7313–7317.

Lawrence et al. (19)85). The genomic organisation and nucleotide sequence of the HLA-SB(DP) alpha gene Nucleic Acids Res. 13 (20), 7515–7528.

MacDonald, H. R., Casanova, J. L., Maryanski, J. L., Cerottini, J. C. Oligoclonal expansion of major histocompatibility complex class I-restricted cytolytic T lymphocytes during a primary immune response in vivo: direct monitoring by flow cytometry and polymerase chain reaction. *J. Exp. Med.* 177, 1487–1492 (1993).

Madden, D. R., Gorga, J. C., Strominger, J. L. & Wiley, D. C. The structure of HLA-B27 reveals nonamer self-peptides bound in an extended conformation. *Nature* 353, 321–325 (1991).

Martenson, R. E. Myelin basic protein speciation in Experimental Allergic Encephalomyelitis: A useful Model for Multiple Sclerosis. 1984. Alan R. Liss, Inc., 150 Fifth Avenue, New York, N.Y. 10011. pages 511–521.

Matsui, K., Boniface, J. J., Steffner, P., Reay, P. A., Davis, M. M. Kinetics of T-cell receptor binding to peptide/I-$E^K$ complexes: correlation of the dissociation rate with T-cell responsiveness. *Proc. Natl. Acad. Sci. USA*. 91, 12862–12866 (1994).

Matsui, K. et al. Low affinity interaction of peptide-MHC complexes with T cell receptors. *Science* 254, 1788–1791 (1991).

McHeyzer, M. G., Davis, M. M. Antigen specific development of primary and memory T cells in vivo. *Science* 268, 106–111 (1995).

Miltenyi et al. *Cytometry* 11: 231–238 (1990).

Mitragotri et al. Pharmaceutical Research 13 (3): 411–20 (1996).

Moebius, U., Pallai, P., Harrison, S. C. & Reinherz, E. L. Delineation of an extended surface contact area on human CD4 involved in class II MHC binding. *PNAS* 90, 8259–8263 (1993).

Moore et al., (1982). DNA sequence of a gene encoding a BALF/c mouse Ld transplantation antigen. Science 215 (4533), 679–682.

Nag, B., Deshpande, S. V., Sharma, S. D., & Clark, B. R. Cloned T cells internalize peptide from bound complexes of peptide and purified class II major histocompatibility complex antigen. *J. Biol. Chem.* 268, 14360–14366 (1993).

Nag, B., Kendrick, T., Arimilli, S., Yu, S. C., & Sriram, S. Soluble MHC II-peptide complexes induce antigen-specific apoptosis in T cells. *Cell. Immunol.* 170, 25–33 (1996).

Nag, B., Passmore, D., Kendrick, T., Bhayani, H., & Sharma, S. D. N-linked oligosaccharides of murine major histocompatibility complex class II molecule. Role in antigenic peptide binding, T cell recognition, and clonal nonresponsiveness. *J. Biol. Chem.* 267, 22624–22629 (1992).

Nag B., Arimilli S., Mukku P. V. & Astafieva, I. Functionally active recombinant alpha and beta chain-peptide complexes of human major histocompatibility class II molecules. *Journal of Biological Chemistry* 271(17), 10413–10418 (1996).

Nag B. et al. Stimulation of T cells by antigenic peptide complexed with isolated chains of major histocompatibility complex class II molecules. *Proceedings of the National Academy of Sciences of the United States of America* 90(4), 1604–1608 (1993).

Nicolle, M. W. et al. Specific tolerance to an acetylcholine receptor epitope induced in vitro in myasthenia gravis CD4+ lymphocytes by soluble major histocompatibility complex class II-peptide complexes. *J. Clin Invest.* 93, 1361–1369 (1994).

Oksenberg, J. R. et al. Selection of T-cell receptor V-D-J gene rearrangements with specificity for a MBP peptide in brain lesions of MS. *Nature* 362, 68–70 (1993).

Ota, K. et al. T cell recognition of an immunodominant myelin basic protein epitope in multiple sclerosis. *Nature* 346, 183–187 (1990).

Paterson, P. Y. Multiple sclerosis: An immunologic reassessment. *J. Chron. Dis.* 26, 119–125 (1981).

Quill, H. & Schwartz, R. H. Stimulation of normal inducer T cell clones with antigen presented by purified Ia molecules in planer lipid membranes: specific induction of a long-lived state of proliferative nonresponsiveness. *J. Immunol.* 138, 3704–3712 (1987).

Reiner, S. L., Wang, Z. E., Hatam, F., Scott, P., Locksley, R. M. TH1 and TH2 cell antigen receptors in experimental leishmaniasis. *Science* 259, 1457–1460 (1993).

Rhode, P. R. et al. Single-chain MHC class II molecules induce T cell activation and apoptosis. *J. Immunol.* 157, 4885–4891 (1996).

Sambrook et al. (1989). In *Molecular Cloning. A Laboratory Manual*, Cold Spring Harbor, N.Y.

Schepart et al., (1986). The nucleotide sequence and comparative analysis of the H-2Dp class I H-2 gene. J. Immunol. 136 (9), 3489–3495.

Schwartz, R. H. Models of T cell anergy: is there a common molecular mechanism? *J. Exp. Med.* 184, 1–8 (1996)

Service et al. *Science* 277(5330): 1199–1200 (1997).

Sharma, S. D. et al. Antigen-specific therapy of experimental allergic encephalomyelitis by soluble class II major histocompatibility complex-peptide complexes. *PNAS* 88:11465–11469 (1991).

Spack, E. G. et al. Induction of tolerance in experimental autoimmune myasthenia gravis with solubilized MHC class II:acetylcholine receptor complexes. *J. Autoimmun.* 8, 787–807 (1995).

Steinle et al., (1992). Isolation and characterization of a genomic HLA-Cw6 clone. Tissue Antigens 39(3), 134–137.

Steinman, L. Autoimmune disease. *Sci. Am.* 269, 106–114 (1993).

Studier, F. W., A. H. Rosenberg, J. J. Dunn, and J. W. Dubendorff. 1990. Use of T7 RNA polymerase to direct expression of cloned genes. *Methods Enzymol.* 185:60.

Swanborg, R. H. Autoimmune effector cells. V. A monoclonal antibody specific for rat helper T lymphocytes inhibits adoptive transfer of auto-immune encephalomyelitis. *J. Immunol.* 130, 1503–1505 (1983).

Syha, J., Henkes, W. & Reske, K. Complete cDNA sequence coding for the MHC class II RTI.B α-chain of the Lewis rat. *Nuc. Acids. Res.* 17(10), 3985 (1989).

Syha-Jedelhauser, J., Wendling, U. & Reske, K. Complete coding nucleotide sequence of cDNA for the Class II RTI.B β-chain of the Lewis rat. *Biochim. Biophys. Acta* 1089, 414–416 (1991).

Sykulev, Y. et al. Kinetics and affinity of reactions between an antigen-specific T cell receptor and peptide-MHC complexes. *Immunity* 1, 15–22 (1994).

Thompson, D. and Larson, G. Western blots using stained protein gels. *Biotechniques* 12, 656–658 (1992).

Tonnell et al. (1985). Do beta: a new beta chain gene in HLA-D with a distinct regulation of expression. EMBO J. 4 (11), 2839–2847.

Vandenbark, A. A., Vainiene, M., Celnik, B., Hashim, G. A., Buenafe, A. C. & Offner, H. Definition of encephalitogenic and immunodominant epitopes of guinea pig myelin basic protein (Gp-BP) in Lewis rats tolerized neonatally with Gp-BP peptides. *J. Immunol.* 15, 852–861 (1994).

Vandenbark, A. A., Hashim, G. & Offner, H. Immunization with a synthetic T-cell receptor V-region peptide protects against experimental autoimmune encephalomyelitis. *Nature* 341, 541–544 (1989).

Vandenbark, A. A., Gill, T. & Offner, H. A myelin basic protein specific T lymphocyte line which mediates EAE. *J. Immunol.* 135, 223–228 (1985).

Veillette, A., Bookman, M. A., Horak, E. M. & Bolen, J. B. The CD4 and CD8 T cell surface antigens are associated with the internal membrane tyrosine-protein kinase $p56^{lck}$. *Cell* 55, 301–308 (1988).

Walker, P. R., Ohteki, T., Lopez, J. A., MacDonald, H. R., Maryanski, J. L. Distinct phenotypes of antigen-selected CD8 T cells emerge at different stages of an in vivo immune response. *J. Immunol.* 155, 3443–3452 (1995).

Walter et al., (1994). Sequence, expression, and mapping of rat Mhc class Ib gene. Immunogenetics 39 i5), 351–354.

Walter et al., (1995). Genomic organization and sequence of the rat major histocompatibility complex class Ia gene RT1.Au Immunogenetics 41 (5), 332.

Wegmann K W, Zhao W., Griffin A C., and Hickey W F. Identification of myocarditogenic peptides derived from cardiac myosin capable of inducing experimental allergic myocarditis in the Lewis rat. The utility of a class II binding motif in selecting self-reactive peptides. *J. Immunol.* 153(2), 892–900 (1994).

Weinberg, A. D. et al. Target organ specific upregulation of the MRC OX40 marker and selective production of Th1 lymphokine mRNA by encephalitogenic T helper cells isolated from the spinal cord of rats with experimental autoimmune encephalomyelitis. *J. Immunol.* 152, 4712–5721 (1IS94).

Weinberg, A. D. et al. TGF-β enhances the in vivo effector function and memory phenotype of Ag-specific T helper cells in EAE. *J. Immunol.* 148, 2109–2117 (1992).

Weiner, H. L. et al. Double-blind pilot trial of oral tolerization with myelin antigens in MS. *Science* 259, 1321–1324 (1993).

White, J., M. Blackman, J. Bill, J. Kappler, P. Marrack, D. P. Gold and W. Born. 1989. Two better cell lines for making hybridomas expressing specific T cell receptors. *J. Immunol.* 143:182.2.

Yednock, T. A. et al. Prevention of experimental autoimmune encephalomyelitis by antibodies against α4/β1 integrin. Nature 356, 63 (1992).

Zhao, B., Carson, M., Ealick, S. E. & Bugg, C. E. Structure of scorpion toxin variant-3 at 1.2 angstroms resolution. J. Mol. Biol. 227, 239 (1992).

Zinn-Justin, S., Guenneugues, M., Drakopoulou, Gilquin, B., Vita, C. & Menez, A. Transfer of a beta-hairpin from the functional site of snake curaremimetic toxins to the alpha/beta scaffold of scorpion toxins: Three-dimensional solution structure of the chimeric protein. *Biochemistry* 35(26): 8535–43 (1996).

What is claimed is:

1. A method for detecting or quantifying in a biological sample the presence of T-cells having a receptor specific for a specified antigen, comprising:

combining the biological sample with a recombinant polypeptide comprising covalently linked α1 and β1 domains of a mammalian MHC class II molecule wherein the carboxy terminus of the β1 domain is covalently linked to the amino terminus of the α1 domain, and further comprising the specified antigen bound in a peptide binding groove formed by said α1 and β1 domains, and wherein the recombinant polypeptide does not include an α2 or a β2 domain; and detecting or quantifying in the biological sample the presence of specific binding of the recombinant polypeptide by T-cells having a receptor specific for the specified antigen.

2. The method of claim 1, wherein the specified antigen bound in a peptide binding groove is covalently linked to the amino terminus of the $β_1$ domain.

3. The method of claim 2, wherein the specified antigen is a peptide antigen.

4. The method of claim 2, wherein the covalent linkage between the $β_1$ domain and the specified antigen is provided by a peptide linker sequence.

5. The method of claim 1, wherein an the specified antigen is, associated with the polypeptide by non-covalent interaction.

6. The method of claim 1, wherein the recombinant polypeptide further comprises a covalently linked detectable marker or toxic moiety.

7. The method of claim 1, wherein the covalent linkage between the α1 and β1 domains is provided by a peptide linker sequence.

8. A method for separating T-cells having a receptor specific for a specified antigen from a mixture of cells, comprising:

combining the cell mixture with a recombinant polypeptide comprising covalently linked α1 and β1 domains of a mammalian MHC class II molecule wherein the carboxy terminus of the β1 domain is covalently linked to the amino terminus of the α1 domain, and further comprising the specified antigen bound in a peptide binding groove formed by said α1 and β1 domains, and wherein the recombinant polypeptide does not include an α2 or a β2 domain; and separating those cells bound to the recombinant polypeptide from unbound cells.

9. The method of claim 8, wherein the specified antigen bound in a peptide binding groove is covalently linked to the amino terminus of the $β_1$ domain.

10. The method of claim 8, wherein the specified antigen is a peptide antigen.

11. The method of claim 9, wherein the covalent linkage between the $β_1$ domain and the specified antigen is provided by a peptide linker sequence.

12. The method of claim 8, wherein an the specified antigen is associated with the polypeptide by non-covalent interaction.

13. The method of claim 8, wherein the recombinant polypeptide further comprises a covalently linked detectable marker or toxic moiety.

14. The method of claim 8, wherein the covalent linkage between the α1 and β1 domains is provided by a peptide linker sequence.

* * * * *